US012667377B2

(12) United States Patent
Gill et al.

(10) Patent No.: US 12,667,377 B2
(45) **Date of Patent: \*Jun. 30, 2026**

(54) SUBCUTANEOUS WOUND DEBRIDEMENT

(71) Applicant: Tenex Health, Inc., Malvern, PA (US)

(72) Inventors: Jagjit Singh Gill, Rochester, MN (US); Lewis Hillel Freed, Scottsdale, AZ (US); Bernard Francis Morrey, Fayetteville, TX (US)

(73) Assignee: Tenex Health, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/933,313

(22) Filed: Sep. 19, 2022

(65) Prior Publication Data

US 2023/0181202 A1 Jun. 15, 2023

Related U.S. Application Data

(63) Continuation of application No. 16/872,132, filed on May 11, 2020, now Pat. No. 11,457,937, which is a continuation of application No. 15/973,344, filed on May 7, 2018, now Pat. No. 10,709,461, which is a continuation of application No. 14/475,129, filed on Sep. 2, 2014, now Pat. No. 9,962,181.

(51) Int. Cl.
*A61B 17/22* (2006.01)
*A61B 17/32* (2006.01)

(52) U.S. Cl.
CPC .................. *A61B 17/22012* (2013.01); *A61B 17/320068* (2013.01); *A61B 2217/005* (2013.01); *A61B 2217/007* (2013.01)

(58) Field of Classification Search
CPC ...... A61B 17/22012; A61B 17/320068; A61B 2217/005; A61B 2217/007
See application file for complete search history.

(56) References Cited

U.S. PATENT DOCUMENTS

| | | | |
|---|---|---|---|
| 3,575,622 A | 4/1971 | Nielson et al. | |
| 3,589,363 A | 6/1971 | Banko et al. | |
| 3,615,366 A | 10/1971 | Allen | |
| 3,645,725 A | 2/1972 | Denhard, Jr. et al. | |
| 3,668,758 A | 6/1972 | Krock et al. | |
| 3,990,452 A | 11/1976 | Murry et al. | |

(Continued)

FOREIGN PATENT DOCUMENTS

| | | |
|---|---|---|
| CN | 2402273 Y | 10/2000 |
| CN | 2774407 Y | 4/2006 |

(Continued)

OTHER PUBLICATIONS

"Brazing", Wikipedia, accessed Sep. 7, 2017, (definition) in 22 pages. URL: http://en.wikipedia.org/wiki/Brazing.

(Continued)

*Primary Examiner* — Andrew Restaino
(74) *Attorney, Agent, or Firm* — Knobbe, Martens, Olson & Bear LLP

(57) ABSTRACT

Disclosed herein are devices and methods of percutaneously treating an ulcerated wound using ultrasonic energy. Some methods include delivering ultrasonic energy to a target tissue located at a position subcutaneous to the ulcerated wound. In some methods, the ultrasonic energy is delivered using an ultrasonic energy delivery device.

19 Claims, 16 Drawing Sheets

(56)                    References Cited

U.S. PATENT DOCUMENTS

| | | | |
|---|---|---|---|
| 4,120,206 A | 10/1978 | Rud, Jr. |
| 4,188,952 A | 2/1980 | Loschilov et al. |
| 4,227,420 A | 10/1980 | Lamadrid |
| 4,428,748 A | 1/1984 | Peyman et al. |
| 4,515,583 A | 5/1985 | Sorich |
| 4,531,934 A | 7/1985 | Kossovsky et al. |
| 4,535,635 A | 8/1985 | Claren et al. |
| 4,555,952 A | 12/1985 | Jenkins |
| 4,750,902 A | 6/1988 | Wuchinich et al. |
| 4,827,911 A | 5/1989 | Broadwin et al. |
| 4,867,141 A | 9/1989 | Nakada et al. |
| 4,870,953 A | 10/1989 | DonMicheal et al. |
| 4,886,060 A | 12/1989 | Wiksell |
| 4,920,954 A | 5/1990 | Alliger et al. |
| 4,972,705 A | 11/1990 | Fryer et al. |
| 4,979,952 A | 12/1990 | Kubota et al. |
| 5,038,756 A | 8/1991 | Kepley |
| 5,042,461 A | 8/1991 | Inoue et al. |
| 5,108,411 A | 4/1992 | McKenzie |
| 5,139,509 A | 8/1992 | Fischer et al. |
| 5,176,677 A | 1/1993 | Wuchinich |
| 5,267,954 A | 12/1993 | Nita |
| 5,275,607 A | 1/1994 | Lo et al. |
| 5,337,601 A | 8/1994 | Becker et al. |
| 5,344,395 A | 9/1994 | Whalen et al. |
| 5,392,653 A | 2/1995 | Zanger et al. |
| 5,400,646 A | 3/1995 | Kraus et al. |
| 5,403,276 A | 4/1995 | Schechter et al. |
| 5,413,556 A | 5/1995 | Whittingham |
| 5,417,654 A | 5/1995 | Kelman |
| 5,480,379 A | 1/1996 | La Rosa |
| 5,514,086 A | 5/1996 | Parisi et al. |
| 5,520,633 A | 5/1996 | Costin |
| 5,557,972 A | 9/1996 | Jacobs et al. |
| 5,562,609 A | 10/1996 | Brumbach |
| 5,580,347 A | 12/1996 | Reimels |
| 5,609,602 A | 3/1997 | Machemer et al. |
| 5,626,563 A | 5/1997 | Dodge et al. |
| 5,661,245 A | 8/1997 | Svoboda et al. |
| 5,683,406 A | 11/1997 | Altobelli et al. |
| 5,746,720 A | 5/1998 | Stouder et al. |
| 5,747,953 A | 5/1998 | Philipp |
| 5,753,820 A | 5/1998 | Reed et al. |
| 5,814,016 A | 9/1998 | Valley |
| 5,832,412 A | 11/1998 | Guez |
| 5,897,524 A | 4/1999 | Wortrich et al. |
| 5,910,110 A | 6/1999 | Bastable |
| 5,911,700 A | 6/1999 | Mozsary et al. |
| 5,935,096 A | 8/1999 | Barrett |
| 5,983,727 A | 11/1999 | Wellman et al. |
| 5,984,915 A | 11/1999 | Loeb et al. |
| D418,916 S | 1/2000 | Bastable |
| 6,028,387 A | 2/2000 | Boukhny |
| 6,033,375 A | 3/2000 | Brumbach |
| 6,058,779 A | 5/2000 | Cole |
| 6,077,285 A | 6/2000 | Boukhny |
| 6,090,123 A | 7/2000 | Culp et al. |
| 6,102,046 A | 8/2000 | Weinstein |
| 6,139,518 A | 10/2000 | Mozsary et al. |
| 6,176,941 B1 | 1/2001 | Jewett et al. |
| 6,206,014 B1 | 3/2001 | Cameron et al. |
| 6,214,017 B1 | 4/2001 | Stoddard et al. |
| 6,234,993 B1 | 5/2001 | Terpillowski et al. |
| 6,261,249 B1 | 7/2001 | Talish et al. |
| 6,270,471 B1 | 8/2001 | Hechel et al. |
| 6,311,084 B1 | 10/2001 | Cormack et al. |
| 6,379,351 B1 | 4/2002 | Thapliyal et al. |
| 6,402,769 B1 | 6/2002 | Boukhny |
| 6,437,266 B1 | 8/2002 | Pannenborg et al. |
| 6,461,301 B2 | 10/2002 | Smith |
| 6,478,681 B1 | 11/2002 | Overaker et al. |
| 6,499,358 B1 | 12/2002 | Hogan et al. |
| 6,524,251 B2 | 2/2003 | Rabiner et al. |
| 6,551,337 B1 | 4/2003 | Rabiner et al. |
| 6,562,054 B1 | 5/2003 | Weber et al. |

| | | | |
|---|---|---|---|
| 6,602,227 B1 | 8/2003 | Cimino et al. |
| 6,623,444 B2 | 9/2003 | Babaev |
| 6,660,013 B2 | 12/2003 | Rabiner et al. |
| 6,695,781 B2 | 2/2004 | Rabiner et al. |
| 6,695,782 B2 | 2/2004 | Ranucci et al. |
| 6,830,556 B2 | 12/2004 | Harmon et al. |
| 6,941,813 B2 | 9/2005 | Boukhny et al. |
| 6,955,073 B2 | 10/2005 | Morgan et al. |
| 6,964,647 B1 | 11/2005 | Babaev |
| 6,980,419 B2 | 12/2005 | Smith et al. |
| 7,077,820 B1 | 7/2006 | Kadziauskas et al. |
| 7,178,402 B2 | 2/2007 | Wanka et al. |
| 7,204,825 B2 | 4/2007 | Cimino et al. |
| 7,270,656 B2 | 9/2007 | Gowda et al. |
| 7,507,212 B2 | 3/2009 | Tsuchiya et al. |
| 7,614,878 B2 | 11/2009 | Paschke et al. |
| 7,785,278 B2 | 8/2010 | Babaev |
| 7,845,235 B2 | 12/2010 | Sandu et al. |
| 7,850,707 B2 | 12/2010 | Yaguchi et al. |
| 7,931,611 B2 | 4/2011 | Novak et al. |
| 8,011,905 B2 | 9/2011 | Artsyukhovich et al. |
| 8,025,672 B2 | 9/2011 | Novak et al. |
| 8,038,619 B2 | 10/2011 | Steinbacher |
| 8,052,701 B1 | 11/2011 | Cox et al. |
| 8,070,711 B2 | 12/2011 | Bassinger et al. |
| 8,075,503 B2 | 12/2011 | Jaeb |
| 8,115,366 B2 | 2/2012 | Hoffman et al. |
| 8,118,823 B2 | 2/2012 | Cotter et al. |
| 8,303,505 B2 | 11/2012 | Webler |
| 8,382,782 B2 | 2/2013 | Robertson et al. |
| 8,486,032 B2 | 7/2013 | Seegert et al. |
| 8,518,066 B2 | 8/2013 | Cotter et al. |
| 8,545,198 B2 | 10/2013 | Artsyukhovich et al. |
| D698,019 S | 1/2014 | Oliveira |
| 8,679,133 B2 | 3/2014 | Peterson |
| 8,741,953 B2 | 6/2014 | Deshpande et al. |
| 8,790,096 B2 | 7/2014 | Sorensen |
| 9,011,337 B2 | 4/2015 | Slayton et al. |
| 9,017,326 B2 | 4/2015 | DiNardo et al. |
| 9,149,291 B2 | 10/2015 | Parham et al. |
| 9,421,027 B2 | 8/2016 | Cotter et al. |
| 9,482,216 B2 | 11/2016 | Sorensen |
| 9,664,547 B1 | 5/2017 | Koltz, Jr. et al. |
| 9,730,721 B2 | 8/2017 | Gill et al. |
| 9,763,689 B2 | 9/2017 | Parham |
| 9,770,257 B2 | 9/2017 | Parham et al. |
| 9,795,404 B2 | 10/2017 | Gill |
| 9,861,382 B2 | 1/2018 | Smith et al. |
| 9,888,937 B2 | 2/2018 | Gill et al. |
| 9,931,447 B2 | 4/2018 | Layser et al. |
| 9,962,181 B2 | 5/2018 | Gill et al. |
| 9,968,371 B2 | 5/2018 | Todd |
| 9,993,259 B2 | 6/2018 | Barnes et al. |
| 10,004,481 B2 | 6/2018 | Slayton et al. |
| 10,194,973 B2 | 2/2019 | Wiener et al. |
| 10,335,189 B2 | 7/2019 | Aklog et al. |
| 10,357,272 B2 | 7/2019 | Barnes et al. |
| 10,517,628 B2 | 12/2019 | Parham et al. |
| 10,639,196 B2 | 5/2020 | Kuebler et al. |
| 10,709,461 B2 | 7/2020 | Gill et al. |
| 10,722,619 B2 | 7/2020 | Kuebler et al. |
| 10,864,055 B2 | 12/2020 | Barnes et al. |
| 11,141,186 B2 | 10/2021 | Aklog et al. |
| 11,259,829 B2 | 3/2022 | Barnes et al. |
| 11,259,837 B2 | 3/2022 | Aklog et al. |
| 11,406,415 B2 | 8/2022 | Parham et al. |
| 11,457,937 B2 | 10/2022 | Gill et al. |
| 2002/0007200 A1 | 1/2002 | Desinger |
| 2002/0068930 A1 | 6/2002 | Tasto et al. |
| 2002/0077550 A1 | 6/2002 | Rabiner et al. |
| 2002/0103457 A1 | 8/2002 | Fontayne et al. |
| 2002/0103465 A1* | 8/2002 | Crawford ........ A61B 5/150503 |
| | | 128/919 |
| 2002/0107538 A1* | 8/2002 | Shibata .......... A61B 17/320068 |
| | | 606/169 |
| 2002/0156492 A1 | 10/2002 | Timm et al. |
| 2002/0183720 A1 | 12/2002 | Hill et al. |
| 2003/0158566 A1 | 8/2003 | Brett |
| 2004/0030254 A1 | 2/2004 | Babaev |

(56)     References Cited

U.S. PATENT DOCUMENTS

| | | |
|---|---|---|
| 2004/0082884 A1 | 4/2004 | Pal et al. |
| 2004/0133168 A1 | 7/2004 | Salcudean et al. |
| 2004/0162546 A1 | 8/2004 | Liang et al. |
| 2004/0259483 A1 | 12/2004 | Newell |
| 2004/0267121 A1 | 12/2004 | Sarvazyan et al. |
| 2005/0059939 A1* | 3/2005 | Perkins .............. A61F 9/00745 |
| | | 604/272 |
| 2005/0101984 A1 | 5/2005 | Chanduszko et al. |
| 2005/0119613 A1 | 6/2005 | Moenning et al. |
| 2005/0209560 A1 | 9/2005 | Boukhny et al. |
| 2005/0209621 A1 | 9/2005 | Gordon et al. |
| 2005/0228288 A1 | 10/2005 | Hurst |
| 2005/0234476 A1 | 10/2005 | Whitmore et al. |
| 2006/0027028 A1 | 2/2006 | Ariav et al. |
| 2006/0073048 A1 | 4/2006 | Malackowski |
| 2006/0184071 A1 | 8/2006 | Klopotek |
| 2006/0195106 A1 | 8/2006 | Jones et al. |
| 2006/0241450 A1 | 10/2006 | Da Silva et al. |
| 2006/0293722 A1 | 12/2006 | Slatkine et al. |
| 2007/0250041 A1 | 10/2007 | Werp |
| 2007/0255196 A1 | 11/2007 | Wuchinich |
| 2007/0276352 A1 | 11/2007 | Crocker et al. |
| 2008/0004621 A1 | 1/2008 | Dahla et al. |
| 2008/0004649 A1 | 1/2008 | Babaev |
| 2008/0033349 A1 | 2/2008 | Suzuki |
| 2008/0033410 A1 | 2/2008 | Rastegar et al. |
| 2008/0058648 A1 | 3/2008 | Novak et al. |
| 2008/0058775 A1 | 3/2008 | Darian et al. |
| 2008/0091182 A1 | 4/2008 | Mehta |
| 2008/0097253 A1 | 4/2008 | Pedersen et al. |
| 2008/0154218 A1 | 6/2008 | Gomez et al. |
| 2008/0183109 A1 | 7/2008 | Babaev |
| 2008/0195002 A1 | 8/2008 | Thompson et al. |
| 2008/0234710 A1 | 9/2008 | Neurohr et al. |
| 2008/0294087 A1 | 11/2008 | Steen et al. |
| 2009/0024076 A1 | 1/2009 | Babaev |
| 2009/0030338 A1 | 1/2009 | Crocker et al. |
| 2009/0069712 A1 | 3/2009 | Mulvihill et al. |
| 2009/0112098 A1 | 4/2009 | Vaezy et al. |
| 2009/0312693 A1 | 12/2009 | Thapliyal et al. |
| 2010/0056986 A1 | 3/2010 | Allen et al. |
| 2010/0069825 A1 | 3/2010 | Raney |
| 2010/0076476 A1 | 3/2010 | To et al. |
| 2010/0145258 A1 | 6/2010 | Hertweck |
| 2010/0211083 A1 | 8/2010 | Sauer |
| 2010/0228207 A1 | 9/2010 | Ballakur et al. |
| 2010/0312102 A1 | 12/2010 | Barnes et al. |
| 2011/0015660 A1 | 1/2011 | Wiener et al. |
| 2011/0040212 A1 | 2/2011 | Dietz et al. |
| 2011/0066174 A1 | 3/2011 | Gilbert |
| 2011/0160620 A1* | 6/2011 | Gill .................... A61B 17/3205 |
| | | 601/2 |
| 2011/0251461 A1 | 10/2011 | Gomez Gonzalez et al. |
| 2012/0078164 A1 | 3/2012 | Mulvihill et al. |
| 2012/0083728 A1 | 4/2012 | Sorensen et al. |
| 2012/0209303 A1 | 8/2012 | Frankhouser et al. |
| 2013/0096596 A1 | 4/2013 | Schafer |
| 2013/0267779 A1 | 10/2013 | Woolford et al. |
| 2013/0267892 A1 | 10/2013 | Woolford |
| 2014/0039451 A1 | 2/2014 | Bangera et al. |
| 2015/0018622 A1 | 1/2015 | Tesar et al. |
| 2016/0030685 A1 | 2/2016 | Lane |
| 2016/0096040 A1 | 4/2016 | Parham |
| 2017/0056032 A1 | 3/2017 | Look et al. |
| 2017/0215854 A1 | 8/2017 | Todd |
| 2017/0290598 A1 | 10/2017 | Culbert et al. |
| 2017/0311974 A1 | 11/2017 | Friedrichs |
| 2018/0192194 A1 | 7/2018 | Pompei |
| 2018/0207397 A1 | 7/2018 | Look et al. |
| 2019/0060533 A1 | 2/2019 | Kuebler et al. |
| 2020/0237977 A1 | 7/2020 | Panotopoulos et al. |
| 2020/0268398 A1 | 8/2020 | Gill et al. |
| 2021/0093482 A1 | 4/2021 | Mehta |
| 2021/0369337 A1 | 12/2021 | Aklog et al. |
| 2022/0346825 A1 | 11/2022 | Parham et al. |

FOREIGN PATENT DOCUMENTS

| | | |
|---|---|---|
| CN | 1933786 A | 3/2007 |
| CN | 2879983 Y | 3/2007 |
| CN | 101166464 A | 4/2008 |
| CN | 101332340 A | 12/2008 |
| CN | 101528306 A | 9/2009 |
| EP | 0709077 A2 | 5/1996 |
| EP | 0709077 B1 | 3/2002 |
| EP | 1634542 A1 | 3/2006 |
| WO | WO 02/076312 A2 | 10/2002 |
| WO | WO 03/101308 A1 | 12/2003 |
| WO | WO 2004/020025 A1 | 3/2004 |
| WO | WO 2004/032596 A2 | 4/2004 |
| WO | WO 2006/121737 A2 | 11/2006 |
| WO | WO 2007/143686 A2 | 12/2007 |
| WO | WO 2008/024894 A2 | 2/2008 |
| WO | WO 2008/027223 A2 | 3/2008 |
| WO | WO 2008/040020 A2 | 4/2008 |
| WO | WO 2008/067681 A1 | 6/2008 |
| WO | WO 2008/072527 A1 | 6/2008 |
| WO | WO 2008/101374 A2 | 8/2008 |
| WO | WO 2008/118708 A2 | 10/2008 |
| WO | WO 2008/128829 A1 | 10/2008 |
| WO | WO 2009/105628 A2 | 8/2009 |
| WO | WO 2011/044338 A2 | 4/2011 |
| WO | WO 2011/082219 A1 | 7/2011 |
| WO | WO 2012/019136 A2 | 2/2012 |
| WO | WO 2013/048912 A2 | 4/2013 |
| WO | WO 2013/184798 A1 | 12/2013 |
| WO | WO 2013/188299 A1 | 12/2013 |
| WO | WO 2016/036810 A1 | 3/2016 |
| WO | WO 2016/054563 A1 | 4/2016 |
| WO | WO 2016/183301 A1 | 11/2016 |
| WO | WO 2017/058696 A1 | 4/2017 |

OTHER PUBLICATIONS

"Debridement of a Wound, Infection, or Burn", Winchester Hospital, accessed Oct. 8, 2021 (definition) in 2 pages. URL: https://www.winchesterhospital.org/health-library/article?id=2010813272.

"Needle", Merriam-Webster.com Dictionary, accessed Oct. 14, 2021, (definition) in 6 pages. URL: https://www.merriam-webster.com/dictionary/needle.

"Pathologic", Cambridge Dictionary, accessed Oct. 8, 2021, (definition) in 4 pages. URL: https://dictionary.cambridge.org/dictionary/english/pathologic.

"Pathology", Merriam-Webster.com Dictionary, accessed Oct. 8, 2021, (definition) in 5 pages. URL: https://www.merriam-webster.com/dictionary/pathology.

"Phacoemulsification", Wikipedia, accessed Oct. 11, 2021, (definition) in 2 pages. URL: http://en.wikipedia.org/wiki/Phacoemulsification.

"Resonance", Wikipedia, accessed Oct. 12, 2021, (definition) in 9 pages. URL: https://en.wikipedia.org/wiki/Resonance.

"Stainless Steel—Heat Treatment", AZO Materials, Jan. 2002, in 6 pages. URL: https://www.azom.com/article.aspx?ArticleID=1141.

Armstrong, D. G et al., "Guest Editorial: are diabetes-related wounds and amputations worse than cancer?", International Wound Journal, Dec. 2007, vol. 4(4), pp. 286-287.

Barshes, N. et al., "The system of care for the diabetic foot: objectives, outcomes, and opportunities", Diabetic Foot and Ankle, Oct. 2013, vol. 4, in 12 pages.

Boulton, A. et al., "The global burden of diabetic foot disease", The Lancet, Nov. 2005, vol. 366, pp. 1719-1724.

Declaration under 37 CFR § 1.132 by Tate R. Parham, dated Jan. 20, 2015, in 3 pages.

Driver, V. et al., "The costs of diabetic foot: The economic case for the limb salvage team", Journal of Vascular Surgery, Sep. 2010, vol. 52, pp. 17S-22S.

Edmonds, M. et al., "Diabetic Foot Ulcers", BMJ, Feb. 2006, vol. 332, pp. 407-410. URL: https://www.ncbi.nlm.nih.gov/pmc/articles/PMC137096/.

Espensen, E. H., "Assessing debridement options for diabetic wounds", Podiatry Today, Mar. 2007, vol. 20, Issue 3, pp. 101-106. URL: https://www.podiatrytoday.com/article/6825.

(56)         References Cited

OTHER PUBLICATIONS

Kowalewski et al., Issues in Vacuum Brazing, May 1, 2006, available at https://www.secowarwick.com/assets/Documents/Articles/Vacuum-Furnaces/Issues-in-vacuum-brazing- VAC.pdf.

Labanca, M. et al., "Piezoelectric surgery: twenty years of use", British Journal of Oral and Maxillofacial Surgery, 2008, vol. 46, pp. 265-269.

Lavery, L. A. et al., "Risk factors for foot infections in individuals with diabetes", Diabetes Care, Jun. 2006, vol. 29(6), pp. 1288-1293.

Lin et al., "Clinical Outcomes of Ultrasound-Guided Aspiration and Lavage in Calcific Tendinosis of the Shoulder". HSSJ, 3:99-105 (Feb. 2007), published online 2006.

Hoigne, D. et al., "Piezoelectric osteotomy in hand surgery: first experiences with a new technique", BMC Musculoskeletal Disorders, Apr. 2006, vol. 7(1), in 4 pages.

Margolis, D. et al., "Economic burden of diabetic foot ulcers and amputation: Diabetic Foot Ulcers, Data Points #3", Agency for Healthcare Research and Quality (prepared by the University of Pennsylvania DECIDE Center, under Contract No. HHSA290200500411), Jan. 2011, in 7 pages.

Ramsey, S. D. et al., "Incidence, outcomes, and cost of foot ulcers in patients with diabetes", Diabetes Care, Mar. 1999, vol. 22(3), pp. 382-387.

Skrepnek, G., "Foot-in-wallet disease: Tripped up by 'cost-saving' reductions", Diabetes Care, Sep. 2014, vol. 37, pp. e196-e197.

Smith, J. et al., "Ultrasound Guided Percutaneous Tenotomy for Chronic Lateral Epicondyle Tendinopathy (Tennis Elbow): A Novel Approach Using Mini-Invasive Instrumentation", Dec. 2005, in 22 pages.

Canadian Office Action for CA Application No. 2,959,729, mailed Jul. 2, 2021.

European Extended Search Report for EP Application No. 15837307.6, dated on May 6, 2019.

European Office Action for EP Application No. 15837307.6, dated Jul. 15, 2021.

European Supplementary Search Report for EP Application No. 13805094.3, dated Mar. 22, 2017.

European Supplementary Search Report for EP Application No. 09712545.4, dated Jun. 20, 2011.

European Supplementary Search Report for EP Application No. 09713554.5, dated Apr. 15, 2013.

European Supplementary Search Report for EP Application No. 10841671.0, dated Sep. 5, 2016.

International Search Report and Written Opinion for International Application No. PCT/US2015/053812, dated Dec. 28, 2015.

International Search Report and Written Opinion for International Application No. PCT/US2015/048075, dated Nov. 27, 2015.

International Search Report and Written Opinion for International Application No. PCT/US2013/044989, dated Nov. 6, 2013.

International Search Report and Written Opinion for International Application No. PCT/US2009/034659, dated Oct. 1, 2009.

International Search Report and Written Opinion for International Application No. PCT/US2010/062341, dated Mar. 25, 2011.

International Search Report and Written Opinion for International Application No. PCT/US2016/032055, dated on Sep. 29, 2016.

* cited by examiner

144

145

147

148

145

θ

136

139

144

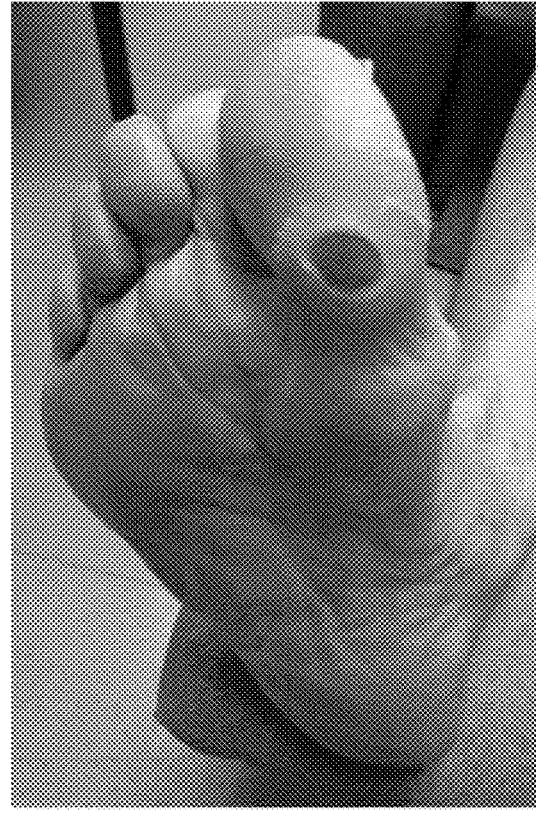
*FIG.13A*                    *FIG.13B*

*FIG.16A*        *FIG.16B*

SUBCUTANEOUS WOUND DEBRIDEMENT

INCORPORATION BY REFERENCE TO ANY PRIORITY APPLICATIONS

This application is a continuation of U.S. application Ser. No. 14/475,129, filed Sep. 2, 2014, the entire contents of which are incorporated herein by reference.

Any and all applications for which a foreign or domestic priority claim is identified in the Application Data Sheet as filed with the present application are hereby incorporated by reference under 37 CFR 1.57.

BACKGROUND

Chronic ulceration of the foot is one of the most common and difficult to treat consequences of diabetes and other neuropathogenic conditions. Diabetic foot ulcerations are noted to occur in 15-25% of diabetic patients in the course of their lifetime. Diabetic foot ulcerations are subject to unopposed repetitive microtrauma, compounded by diabetic systemic comorbidities such as peripheral neuropathy, structural changes, and ischemia. Neuropathic feet are also at risk for a Charcot deformity, which can completely change normal pedal osseous architecture, creating increased foci of plantar pressures at risk for ulceration.

Neuropathic pedal ulcerations from diabetes and other etiologies are common and costly. The statistical morbidity of diabetic foot ulcers is sobering and often overlooked. The diabetic population now numbers over 26 million people in the United States. The global "diabetic foot disease" is "a potentially devastating complication of a disease that is reaching epidemic proportions . . . someone, somewhere, looses a leg because of diabetes every 30 seconds of every day." Andrew Boulton, et al., The global burden of diabetic foot disease, 366. 9498 LANCET 1719 (2005). Diabetics, compared to non-diabetics, are 30 times more likely to suffer a lower extremity amputation over the course of their lives and have a 10 fold greater risk of being hospitalized for bone and soft tissue infections. L A Lavery, et al., Risk factors for foot infections in individuals with diabetes, 29(6) Diabetes Care 1288 (2006). Diabetic foot ulcerations precede 85% of all non-traumatic lower extremity amputations. DG Armstrong et al., Guest editorial: are diabetes-related wounds and amputations worse than cancer?, 4(4) INT'L WOUND J. 286 (December 2007). The five-year mortality after a lower extremity amputation has been shown to be 45%, greater than or equal to that of other deadly cancers (e.g., colon, lung, and pancreatic). Id.

Foot ulcers may result from a number of factors. Contributing factors may include sepsis, arteriopathy, and neuropathy. In some cases, the diabetic condition leads to the generation of avascular tissue at subcutaneous levels or in deep tissue. An avascular condition and patient immobility generally lead to pressure and break-down of the affected tissues. This chronic condition produces break-down of the overlying skin, which may in turn lead to secondary infection.

Recurrent ulcerations become common in neuropathic patients and increase risk of local and systemic infection, repetitive hospitalization, and potential amputation. These wounds can be challenging and have a high rate of recurrence despite successful episodes of wound care.

Current treatments are underwhelming and focus on treating broken skin and address superficial aspects of ulcers. The goal of ulcer treatment is generally to resolve the ulcer and reduce recurrence. To date, the focus of treatment has been on promoting the healing of the superficial aspects of the ulcer at the epidermal level and reducing the bacterial burden. The end result of conventional treatments may be reduction in ulcer size, complete resolution of the ulcer size, or a recurrence of the ulcer.

Moreover, current therapies designed to heal the ulceration are unpredictable, costly and time consuming, and even when successful may not address underlying etiologies of osseous, scar, or bursa origin and thereby often lead to recurrence in the same location. A recurrence rate of 40% over the four months following healing has been cited by consensus panels. The International Diabetes Foundation reports recurrence rates of over 50% after three years, and notes that "costs of diabetic foot disease therefore include not only the immediate episode, but social services, home care, and subsequent ulcers."

Current treatments may be separated into two types: indirect and direct. Indirect treatments include off-loading of weight and/or pressure from the affected area through customized footwear or by using assistive devices, such as crutches, scooters, etc. Direct treatments include debridement of the ulcer surface, topical wound dressing to control the wound bed moisture, and adjunctive methods. Adjunctive methods include grafts/skin substitutes, negative pressure, hyperbaric oxygen, and phototherapy.

Conventional treatments share a number of features. The best outcomes include ulcer healing in 50-70% of cases but with a recurrence rate approaching 100% about three months after the treatment. Most methods are provider intensive in that repeat procedures are required. Patient compliance is also an issue the limits the success of any of these procedures. Ultimately, current procedures are costly.

In addition to the grave considerations of morbidity, neuropathic ulcerations pose a high financial burden. Up to ⅓ of the $116 billion in direct costs generated by the treatment of diabetes and its complications has been attributed to treatment of diabetic foot ulcers (Vickie Driver, et al., The costs of diabetic foot: the economic case for the limb salvage team, 52(3) J. VASCULAR SURGERY 17S (2010)) and annual direct costs of diabetic limb complications are more expensive than five of the most expensive cancers: breast, colorectal, lung, prostate, and leukemia (Neal R. Barshes, et al., The system of care for the diabetic foot: objectives, outcomes, and opportunities, 4 DIABETIC FOOT & ANKLE 21847 (2013)).

A retrospective nested case-control study found that relative cost of care for diabetics with ulcers was 2.4 times higher than diabetics without ulcers prior to ulceration, jumping to 5.4 times higher in the year after the ulcer, and returning to 2.8 times higher two years after the ulcer. Furthermore, the 1999 study showed the excess cost of a diabetic foot ulcer was $26,490 in ulcer patients during the year of the ulcer episode, persisting at $17,245 in the following year, compared to diabetics without ulceration with excess costs of $4927 and $5110 during the same respective time periods measured. SD Ramsey, et al., Incidence, outcomes, and cost of foot ulcers in patients with diabetes, 22(3) DIABETES CARE 382 (1999).

When wound healing is unsuccessful, the costs of amputation and dealing with post amputation care are considerable as well. A 2011 report showed approximately $52,000 is reimbursed annually for a Medicare beneficiary with diabetes and a lower extremity amputation. D. MARGOLIS, ET AL. ECONOMIC BURDEN OF DIABETIC FOOT ULCERS AND AMPUTATION: DIABETIC FOOT ULCERS, DATA POINTS #3 AGENCY FOR HEALTH-CARE RESEARCH AND QUALITY, U.S. DEPT. OF HEALTH AND HUMAN SERVICES (January 2011). In an analysis of a decade of inpatient admissions (2001-2010), Skrepnek found that of the 388.4 million inpatient admissions in the US, 66.1 million involved a diagnosis of diabetes (17%), 2.5 million involved diabetic foot ulcers (4%), and the 10-year total costs of the inpatient national bill was $2.4 trillion for diabetes and $113 billion for diabetic foot ulcers. G. Skrepnek, Foot-in-wallet disease: Tripped up by "cost-saving" reductions, Paper presented at DF Con 2014 (Mar. 20-22, 2014).

Accordingly, a need exists for the further development of systems and methods for effectively treatment wounds, not just foot/ankle ulcers.

SUMMARY

Disclosed herein are devices and methods of percutaneously treating an ulcerated wound using ultrasonic energy. Some methods include delivering ultrasonic energy to a target tissue located at a position subcutaneous to the ulcerated wound. In some methods, the ultrasonic energy is delivered using an ultrasonic energy delivery device. In some embodiments, the device includes a transducer, a horn, and a needle secured to the horn. In some embodiments, the device further includes an aspiration conduit and an irrigation conduit. In some methods, a distal portion of the needle of the ultrasonic energy delivery device is or has been positioned at or around the target tissue using a percutaneous approach.

Some methods further include debriding the target tissue with the ultrasonic energy. Some methods further include removing from the subcutaneous position at least some detritus that may have been produced by the debriding. In some methods, the target tissue comprises at least one of the following: soft tissue and hard tissue. Some methods further include delivering fluid to the subcutaneous position. In some methods, the ultrasonic energy is delivered through the needle. In some methods, the ulcerated wound comprises a foot ulcer.

According to some methods, delivering ultrasonic energy to a target tissue includes inserting the distal portion of the needle through a first access portal via a percutaneous approach, generating ultrasonic energy at the subcutaneous position, and removing the proximal portion from the first access portion; and inserting the distal portion of the needle through a second access portal via a percutaneous approach, generating ultrasonic energy at the subcutaneous position, and removing the proximal portion from the first access portion. In some methods, positioning the distal portion of the needle involves the use of an ultrasound guidance system.

In some methods, the target tissue located at the subcutaneous position comprises ulcerated wound tissue. In some methods, the ulcerated wound tissue comprises bone tissue. In some methods, the ulcerated wound tissue comprises abnormal growth. In some methods, the abnormal growth comprises at least one of a bony prominence, calcific tissue, and necrotic tissue.

According to some embodiments, the needle comprises a stainless steel material, and wherein the needle is brazed to the horn. In some embodiments, the needle is a fully hardened hypodermic needle. In some embodiments, the needle includes an exposed portion having a length of about 0.75 inches to about 1.5 inches. In some embodiments, the needle has a gauge of about 12 to about 25.

Additional features and advantages are described herein, and will be apparent from the following Detailed Description and figures.

BRIEF DESCRIPTION OF THE DRAWINGS

FIGS. 13A-13B illustrate a right plantar hallux ulceration before and after an ultrasonic debridement treatment performed according to the present disclosure.

FIGS. 16A-16B illustrate the left foot of a patient with a failed Charcot reconstruction before and about four weeks after an ultrasonic debridement treatment performed according to the present disclosure.

DETAILED DESCRIPTION

Figure 1:
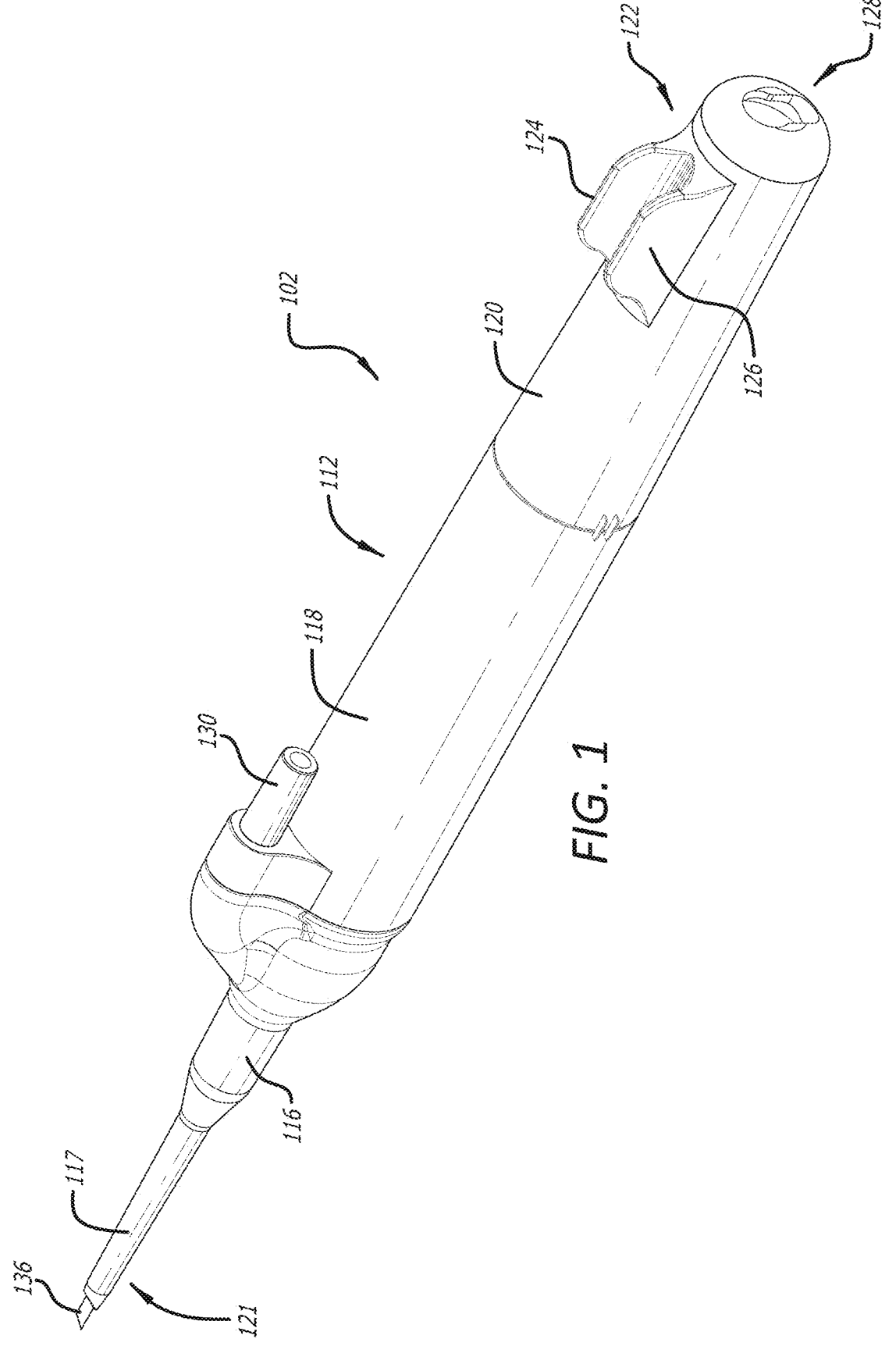
FIG. 1 is a perspective view of an exemplary embodiment of the delivery device disclosed herein, illustrating an example extension and an example tab.

Various embodiments described herein provide systems and methods for accessing and treating target body tissue, such as necrotic, diseased, or infected tissue with or without a bony prominence using ultrasonic energy.

It has been found that different tissues respond to different ultrasonic frequencies. Without being tied to any particular theory, it is believed that a frequency range from about 25 kHz to about 29 kHz effectively removes pathologic subcutaneous tissues, such as necrotic tissue, abnormal bone tissue, wound tissues, etc., because these tissues are generally more dense than normal, healthy tissues. Again, without being limited to any particular theory, it is believed that the density of the unhealthy, abnormal tissues is better able to absorb and be removed by the ultrasonic energy produced by the devices and systems of the present disclosure.

According to some embodiments disclosed herein, an ultrasonic device has been developed that provides a consistent, low-cost, and less invasive treatment option to patients suffering from chronic neuropathic foot ulceration. Using this device and the methods disclosed herein, undesired necrotic tissue, cicatrix, bursa, or abnormal bone is cut or otherwise removed with concomitant removal of the treated diseased tissue.

Ultrasonic energy has the potential to address the three main pathologic characteristics of chronic neuropathic foot ulceration: avascularity, sub-ulcer prominence, and secondary polymicrobial infection. Ultrasonic energy promotes neovascularization in experimental and clinical settings. Furthermore, the handpiece design and the predetermined settings deliver precise focused energy extending approximately 1-2 mm from the tip. This system is bactericidal, and it is hypothesized that the procedure produces a congruent zone of sterilization. Concurrent debridement, irrigation, and aspiration via the same handpiece allow for removal of necrotic tissue, scar, bursa, or any tissue that may be the source of the sub-ulcer prominence. This procedure allows the surgeon to address the wounds from the inside out or deep below the surface to remove pressure-contributing bony prominences, to fenestrate or remove avascular scar or ulcer tissue, and to possibly release growth factors into the area.

Several advantages to the procedure are noteworthy. The probe—which is described in greater detail below—does not enter the wound (thereby lessening the possibility of inoculating to a deeper level), and the entry wounds (which may be about 5 mm) are small enough to not require a sutured closure. The ability to perform the procedure under local anesthetic in a percutaneous fashion to treat the subcutaneous pathologic tissue allows for a wider patient selection on patients with otherwise prohibitive comorbidities or advanced age.

With percutaneous ultrasonic treatment of subcutaneous diseased tissue, functional ambulation without recurrence is a realistic goal. This technique is effective across a wide range of anatomic locations. For example, in the foot, the following anatomical locations may be treated: the heel, the Charcot midfoot, the plantar 1st metatarsalphalangeal joint, the planter central metatarsalphalangeal joint, the hallux, and the interdigital pedal location. In some cases, use of the devices and methods disclosed herein result in complete healing without recurrence.

In wounds that occur more proximally or in areas near vital neurovascular structures, use of visual ultrasound guidance may help avoid those structures and potential adverse sequelae.

In some embodiments, the system includes a delivery device having a stainless steel type needle brazed to a horn using a heating process or brazing process. The brazing or heating processes described herein may allow for an increase in the length of the stainless steel type needles which may be used by a delivery device for accessing and treating target body tissue.

An exemplary system according to the present disclosure may be configured to percutaneously access and act upon target tissue while helping reduce collateral trauma. In some embodiments, using a minimally-invasive ultrasonic system increases the accuracy of removing diseased tissue when compared to surgical procedures that include surgical dissections of healthy tissue. In some embodiments, the percutaneous, minimally-invasive nature of such systems facilitates treatment of a patient under local anesthesia. This is advantageous in several respects, including patient comfort and convenience and avoiding costs associated with operating room time and general anesthesia.

According to the present disclosure, ultrasonic systems may include a delivery device and a controller that is operatively connected to the delivery device. In some embodiments, the delivery device is operatively connected to a controller via a power line, a vacuum line, and/or an irrigation line. The power line may be connected to the controller via a wired connection. In some embodiments, the controller may be configured to communicate with the delivery device via a wireless communication or a combination of a wired communication and a wireless communication.

In some embodiments, the delivery device is configured to transmit ultrasonic energy to a percutaneous ulcerated wound site at a pre-tuned frequency selected to debride ulcerated wound tissue. In some embodiments, the target ulcerated wound tissue comprises subcutaneous necrotic tissue. In some embodiments, the target ulcerated wound tissue comprises abnormal bone tissue, such as a bony prominence or some other growth that may result from excessive pressure. In some embodiments, the target tissue comprises a mixture of both bone tissue and softer, diseased tissue.

Figure 2:
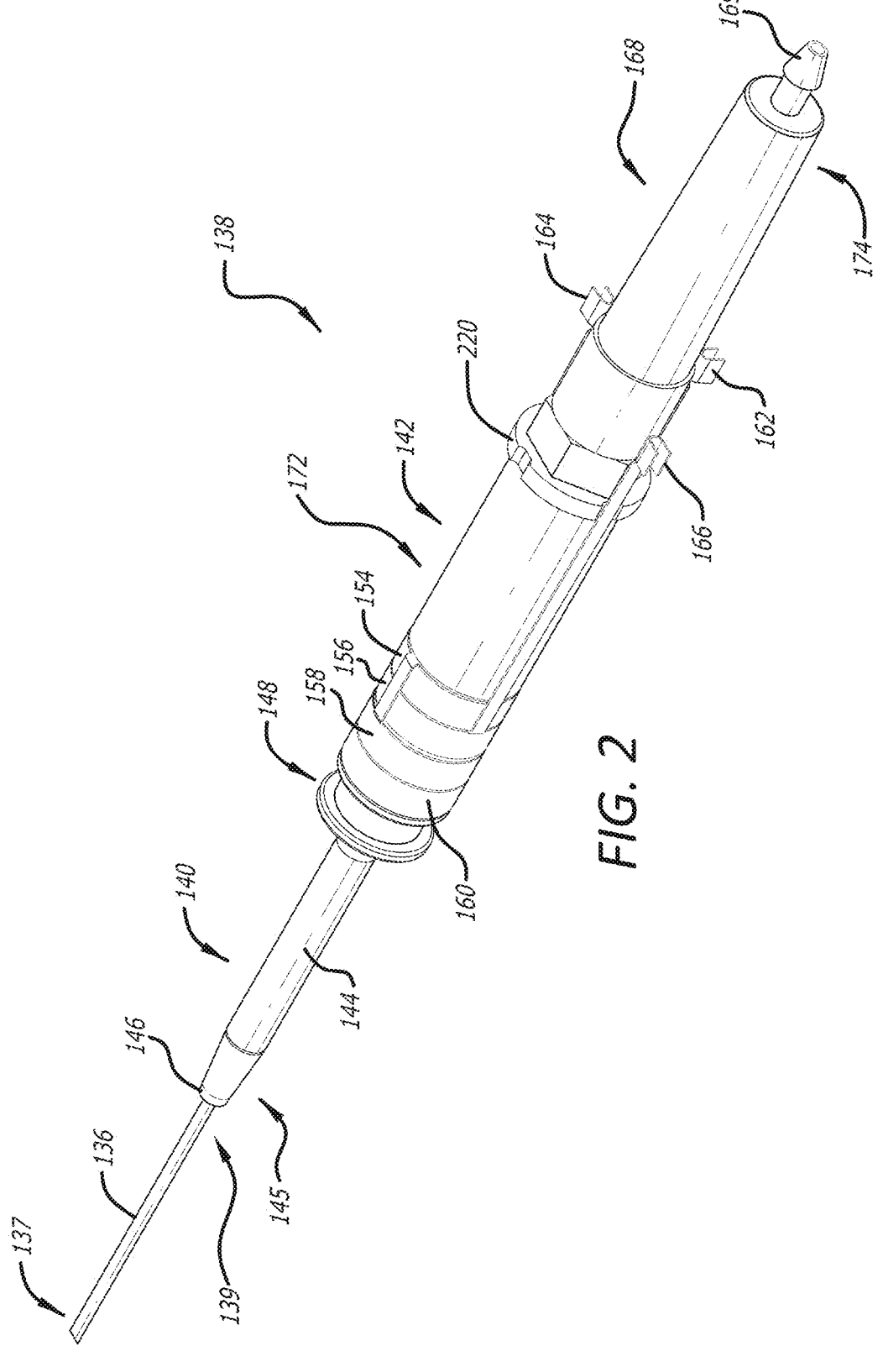
FIG. 2 is a perspective view of an exemplary embodiment of the stack assembly, illustrating the horn assembly, the crystal stack assembly and the compressor.

FIGS. 1 and 2 illustrate a delivery device 102, which according to some embodiments, includes housing 112 and stack assembly 138. In some embodiments, delivery device 102 includes a removable cap over a distal end of delivery device 102.

In some embodiments, housing 112 includes at least two separate portions. For example, as illustrated in FIG. 1, housing 112 includes nose portion 116, body portion 118, and tail portion 120.

In some embodiments, as discussed in more detail below, the housing includes a portion configured to form part of an irrigation conduit. For example, as best illustrated in FIG. 1, nose portion 116 includes portion or sleeve 117. In this example, sleeve 117 defines an inner lumen or channel which forms part of an irrigation conduit.

In some embodiments, sleeve 117 has an insertion portion 121 that extends to a terminal end and is adapted for percutaneous insertion. Insertion portion 121 of sleeve 117 may be any suitable size. In some example embodiments, insertion portion 121 has a size of about twelve gauge or less, about twelve gauge to about twenty-five gauge, or about fourteen gauge to about twenty-two gauge.

In some embodiments, the size of insertion portion 121 is dictated by the procedure in question. For example, in some embodiments where wound tissue in the foot or ankle is to be debrided, insertion portion 121 may exhibit a larger gauge and/or a wider lumen than would be the case or a different procedure. In some embodiments involving wound tissue of the foot, insertion portion 121 may further comprise a stronger material than would otherwise be used. In some embodiments, a wider and/or stronger insertion portion may better debride bone tissue than would a narrower, weaker insertion portion.

Insertion portion 121 may have a lateral width of any suitable size. In some example embodiments, insertion portion 121 has a lateral width of about 2.5 mm or less, about 2.2 mm to about 0.4 mm, or about 2.1 mm to about 0.5 mm. In some embodiments, insertion portion 121 has a lateral width of at least about 2.5 mm.

The length of insertion portion 121 may be any suitable size. In some example embodiments, the length of insertion portion 121 is about three inches to about 0.25 inches, about 2.7 inches to about 0.5 inches, or about 2.5 inches to about 1.0 inch.

In some embodiments, the terminal end of insertion portion 121 is formed with a sharp angle or in some embodiments is squared off.

Insertion portion 121 may leave the exposed portion of needle 136 at any suitable length. In some embodiments, insertion portion 121 may leave the exposed portion of needle 136 at a length of about 10 mm or less, for example between from 2 mm to about 10 mm.

In some embodiments, insertion portion 121 may leave the exposed portion of needle 136 at a length of at least about 7 mm. In some embodiments, the length of the exposed portion is between about 7 mm and about 15 mm. In some embodiments, the exposed portion of needle 136 is at least about 0.75 inches, at least about 1 inch, or at least about 1.5 inches. In some embodiments, the exposed portion of needle 136 is between about 0.75 inches and about 1.5 inches, between about 0.9 inches and about 1.1 inches, or between about 1 inch and about 1.05 inches. In some embodiments, the exposed portion of needle 136 is about 1.032 inches.

In some embodiments, as best illustrated in FIG. 1, sleeve 117 may be integrally formed as part of nose portion 116. In some embodiments, needle sleeve 117 is separate from and connects to nose portion 116.

Sleeve 117 may be formed of a biocompatible material suitable for dampening products of ultrasonic energy (e.g., heat and vibration). In some embodiments, sleeve 117 is coated with an echogenic material. In some embodiments, sleeve 117 is formed of a material exhibiting a differential echogenicity to that of needle 136. In such embodiments, both needle 136 and sleeve 117 facilitate ultrasonic imaging and separate identification during percutaneous insertion.

In some embodiments, nose portion 116 is configured to function as a guide for needle 136 during ultrasonic vibration.

Figure 9:
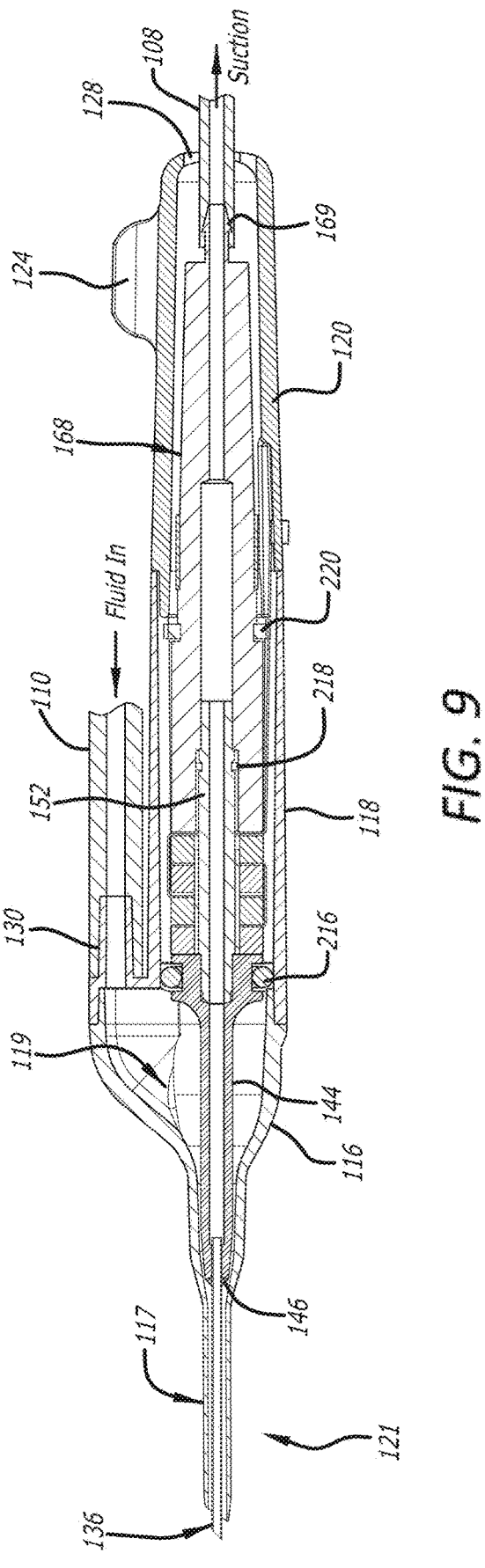
FIG. 9 is a cross-sectional view of one example of a delivery device, illustrating the irrigation conduit and the vacuum conduit.

In some embodiments, as illustrated in FIG. 9 and discussed in more detail below, nose cone portion 116 defines channel 119 for enabling and/or directing fluid flow into an incision site. The fluid flow may act to remove heat buildup caused by friction.

In some embodiments, to prevent or limit air from being delivered to an ulcerated wound tissue site from the irrigation conduit, an ultrasonic system is configured to evacuate air from the irrigation conduit. Nose portion 116 may be formed from substantially clear material which allows a user to determine whether any air bubbles exist in the irrigation conduit.

In some embodiments, housing 112 may define a portion to facilitate a connection to irrigation line 110. For example, as best illustrated in FIG. 1, body portion 118 defines extension 130 which enables delivery device 102 to connect to irrigation line 110. In some embodiments, as best illustrated in FIG. 1, extension 130 defines a hollow lumen having an inlet.

Extension 130 may be configured such that irrigation line 110 slides over the outer surface of extension 130. The outside surface of extension 130 may have a luer type taper on the outside surface of extension 130 which is configured to connect to irrigation line 110.

Extension 130 may have any suitable shaped cross section, such as, for example, a cylindrical cross section or a substantially square-shaped cross section. In this example, extension 130 forms part of the irrigation conduit. In another example, extension 130 may have a barb fitting to connect to irrigation line 110. In some embodiments, extension 130 may be referred to as a tube fitting.

As illustrated in FIG. 1 and discussed in more detail below, in some embodiments, tail portion 120 defines opening 128 which allows vacuum line 108 and power line 106 to connect to delivery device 102.

In some embodiments, housing 112 has a substantially cylindrical-shaped cross section. In some embodiments, housing 112 may a different shaped cross section, such as, for example a substantially square-shaped cross section.

The above-described separate portions of housing 112 may be configured to connect to each other using any suitable method. For example, in some embodiments, using glue, nose portion 116 may be configured to mate with and connect to a first end of body portion 118, and tail portion 120 may be configured to mate with and connect to the opposite end of body portion 118.

Housing 112 may be formed of any suitable material including molded plastic and/or acrylonitrile butadiene styrene.

In an embodiment where housing 112 is designed to include separate portions such as the portions described above, this design may provide a cost effective method for producing a low cost ultrasonic hand piece.

A cap may be configured to be removably connected to housing 112. For example, a cap may be connected to nose portion 116 and removed prior to performing a debridement procedure. In some embodiments, the cap is configured to removably connect to nose portion 116 by employing a luer taper interface.

In some embodiments, the cap is configured to seal the fluid system of an ultrasonic system. Such a configuration enables the ultrasonic system to be primed and prepared for surgery.

In some embodiments, as best illustrated in FIG. 2, stack assembly 138 includes horn assembly 140, crystal stack assembly 142, and compressor 168.

Figure 6:
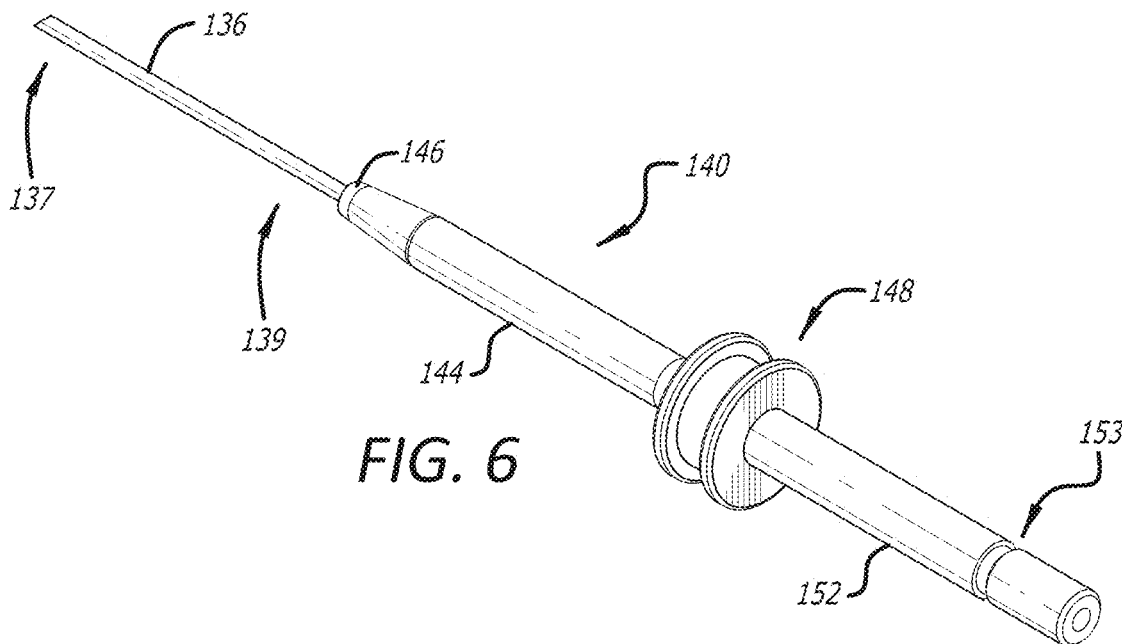
FIG. 6 is a perspective view of an exemplary horn assembly, illustrating the horn assembly being connected to the mounting member.

In some embodiments, delivery device 102 includes a mounting member. For example, as illustrated in FIG. 6, delivery device 102 includes mounting member 152.

Figure 5:
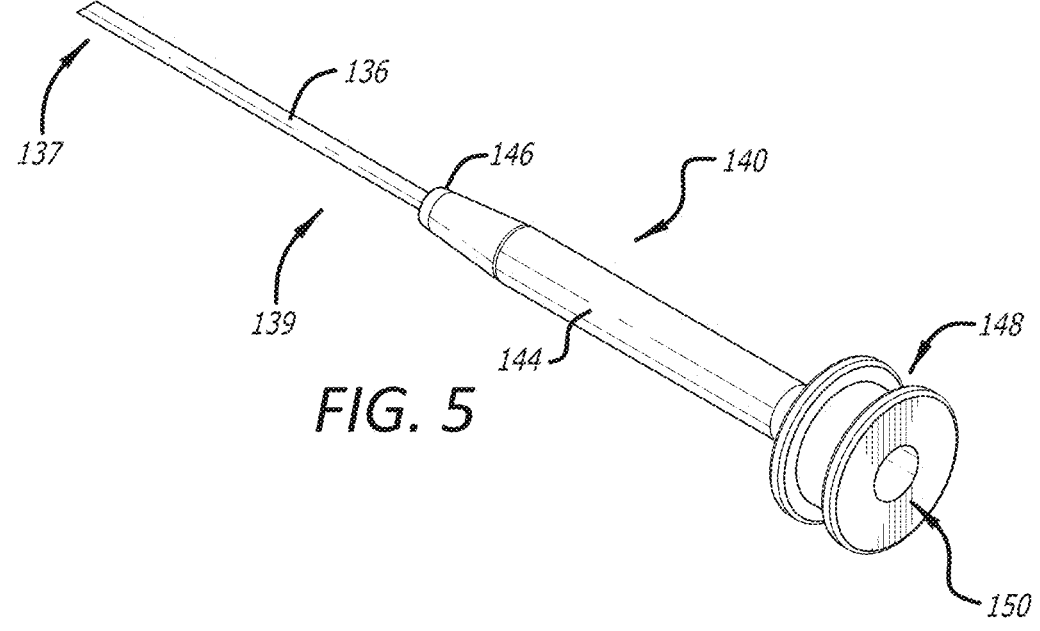
FIG. 5 is a perspective view of an exemplary horn assembly, illustrating the horn having an opening for connecting to the mounting member.

In some embodiments, horn assembly 140 is configured to connect to mounting member 152. For example, as illustrated in FIG. 5, in some embodiments, opening 150 may define a threaded portion which is configured to mate with and connect to a threaded portion of mounting member 152. FIG. 6 illustrates one example of mounting member 152 being connected to horn assembly 140. It should be appreciated that horn assembly 140 may connect to mounting member 152 in any suitable manner.

In some embodiments, horn assembly 140 includes mounting member 152. That is, in these embodiments, mounting member 152 is not a separate component of horn assembly 152, but rather is formed as a single, integral component of horn assembly 152. For example, horn 144 and mounting member may be formed as a single component.

In some embodiments, horn assembly 140 includes needle 136 and horn 144. In some embodiments, needle 136 is a generally hollow tubular member which defines a lumen. As illustrated in FIGS. 2, 5, and 6, needle 136 may have distal portion 137 and proximal portion 139.

Distal portion 137 is preferably adapted for percutaneous insertion. Distal portion 137 may be formed at a sharp angle or may be squared off. In some embodiments, distal portion 137 may have serrated edges or other surface features for enhancing ultrasonic debridement.

Distal portion 137 may have any suitable size. In some example embodiments, distal portion 137 has a size of about 12 gauge or less, about 12 gauge to about 25 gauge, or about 14 gauge to about 22 gauge.

Distal portion 137 has a lateral width of any suitable size. In some example embodiments, display portion 137 has a lateral width of about 2.5 mm or less, about 2.2 mm to about 0.4 mm, or about 2.1 mm to about 0.5 mm.

According to some embodiments, distal portion 137 has an inner and an outer diameter of any suitable size. In some embodiments, the inner diameter is between about 0.03 inches and about 0.1 inches, between about 0.05 inches and about 0.08 inches, between about 0.06 inches and about 0.07 inches. In some embodiments, the inner diameter of distal portion 137 is about 0.063 inches. In some embodiments, the outer diameter is between about 0.04 inches and about 0.15 inches, between about 0.06 inches and about 0.1 inches, between about 0.07 inches and about 0.08 inches. In some embodiments, the outer diameter of distal portion 137 is about 0.076 inches.

The length of distal portion 137 may be any suitable size. In some example embodiments, the length of distal portion 137 is about 3 inches to about 0.25 inches, about 2.7 inches to about 0.5 inches, or about 2.5 inches to about one inch.

In some embodiments, needle 136 is formed of an echogenic, biocompatible material suitable for conveying ultrasonic energy. For example, needle 136 may be formed of a stainless steel alloy. In some embodiments, needle 136 may include a stainless steel hypodermic needle. In some embodiments, needle 136 may be formed from a 174 precipitant hardened stainless steal. In some embodiments, needle 136 includes a heat hardened stainless steal. In some embodiments, needle 136 includes a work hardened stainless steal, such as 300 stainless steel.

In some embodiments, needle 136 may have a bevel of about forty-five degrees to facilitate insertion into the surgical site.

In some embodiments, as best illustrated in FIG. 1, sleeve 117 and needle 136 are positioned such that needle 136 has a covered portion and an exposed portion.

In some embodiments, sleeve 117 may be configured to reduce unwanted, collateral transmission of heat, ultrasonic energy, or other byproducts of the ultrasonic energy being conveyed along the covered portion of needle 136. Sleeve 117 may reduce or eliminates damage to non-target body tissues as a result of unwanted transmission of ultrasonic energy.

In operation, needle 136 vibrates at the surgery site and breaks up certain tissue such as scarred tendon tissue, osteophytes, boney prominences, and calcifications. Needle 136 may be configured to direct the aspiration flow from the bore of needle 136 back to collector 192.

Figure 3:
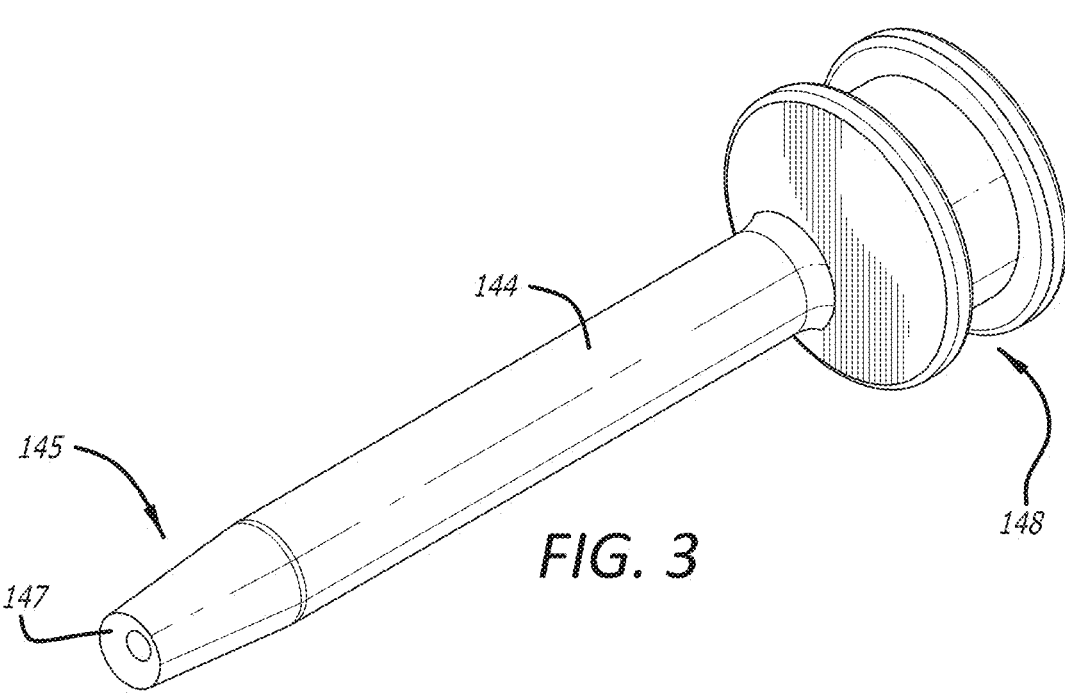
FIG. 3 is an enlarged perspective view of an exemplary horn, illustrating the horn having a groove portion and a slanted tip portion.
Figure 4:
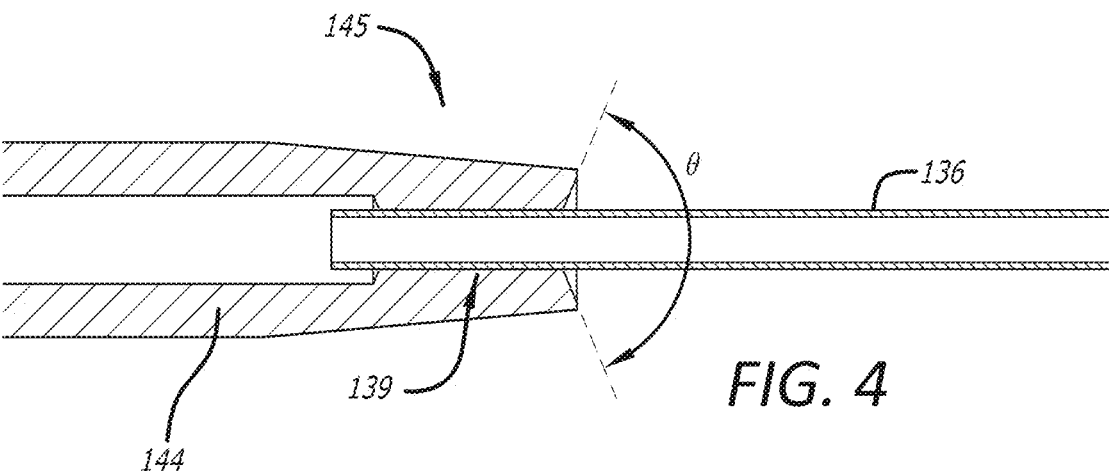
FIG. 4 is a longitudinal section of a portion of the horn assembly, illustrating the slanted tip portion having an angle of about 135.degree.

In some embodiments, horn 144 is configured to compress piezoelectric crystals and amplify ultrasonic vibration. In some embodiments, horn assembly 140 may have a tip portion configured to enable or allow for a more durable connection between horn assembly 140 and needle 136. For example, as illustrated in FIGS. 3 and 4, horn assembly 140 has tip portion 145. In this example, tip portion 145 defines slant portion 147 having an angle ("θ."). In one example, θ. is about 135.degree. Slant portion 147 enables for a more durable connection between horn assembly 140 and needle 136. In this example, slant portion 147 slants inwardly. In this example, this cupped-shaped portion allows for the brazing material to pool into said portion.

In some embodiments, horn 144 defines an opening to connect to other components of delivery device 102. For example, as illustrated in FIG. 5, horn assembly 140 defines opening 150 which enables horn assembly 140 to receive mounting member 152. In one example, mounting member 152 connects to horn 144 via a threaded connection. It should be appreciated that mounting member 152 may connect to horn 144 in any manner.

In some embodiments, as described above, horn assembly 140 includes horn 144 and needle 136. In some embodiments, horn assembly 140 includes horn 144, needle 136 and mounting member 152. In some embodiments, horn 144 and mounting member 152 are formed as a single integral component.

Horn 144 may be made of a metal such as stainless steel. In some embodiments, both horn 144 and needle 136 are made of only stainless steal.

In some embodiments, mounting member 152 defines a bore or lumen that forms a portion of the vacuum conduit and directs aspiration flow from horn assembly 140 to a lumen defined by compressor 168.

In some embodiments, mounting member 152 is made from titanium, which may allow for stack assembly 138 to resonate at a proper frequency (e.g., between about 25 KHz and about 30 KHz). In some embodiments, the desired frequency is between about 25 kHz and about 29 kHz.

Mounting member 152 may be frictionally fit, adhered, welded, or otherwise secured within housing 112. In some embodiments, crystal stack assembly 142 is disposed around mounting member 152.

In some embodiments, using a material (e.g., a brazing material), needle 136 is connected to horn assembly 140 by employing a brazing process or a heating process. During the brazing process, the brazing material melts the brazing material to cause needle 136 to join together with horn 144 to form a single contiguous horn assembly. The melting temperature of the brazing material alloy is preferably low enough such that needle 136 will not anneal during the brazing process. The melting temperature of the brazing material facilitates fixing the needle to the horn.

During the brazing process, needle 136 may be in a condition that can be affected by an elevated temperature. If needle 136 anneals during a brazing process or heating process, then strength of needle 136 is reduced, and needle 136 will likely break during ultrasonic vibration. Because needle 136 cannot anneal, needle 136 cannot be brazed to horn 144 in a vacuum braze environment.

In some embodiments, using the brazing process described herein, needle 136 may be brazed to horn 144 such that needle 136 will not annealed during the brazing or heating process.

For example, in one example, needle 136 and horn 144 may be formed of stainless steel. In this example, needle 136 and horn 144 may be joined together using an acid flux and inert gas (e.g., nitrogen) to facilitate the brazing material flow during the brazing process. In some embodiments, needle 136 is brazed to horn 144 using an induction brazing machine which employs heat generated from an electromagnetic field created by the alternating current from an induction coil. In some embodiments, the braze joint—which may be located in some embodiments at slant portion 147—is protected against oxidation by placing a tube over the braze joint. After the tube is placed over the brazed joint, gas may be added. In some embodiments, an additive (e.g., acid flux) may be used to break surface tension of the metal of needle 136 and the horn 144.

The brazing or heating processes described herein may increase the sizes of the stainless steel type needles which may be used by a delivery device to function properly. In certain delivery devices having certain types of stainless steel needles attached to a horn, the stainless steel needle may break based on the needle's strength. For example, where a stainless steel needle has a length of about twenty-two times the diameter of the bore diameter, it has been found that the manufacturability decreases and the costs substantially increase. Although, a titanium type needle may be used in certain situations to increase the length of the needle, a titanium type needle is significantly more expensive than a stainless steel type needle. Using the brazing or heating procedure described herein, delivery device 102 may include a stainless steel needle having a length of about one thousand times the diameter of the bore. Such a configuration may provide for reduced cost of delivery device 102 by eliminating components typically used in the construction of a delivery device (e.g., a titanium needle).

In some embodiments, the brazing material may include an alloy, nickel, silver, copper and/or a silver based alloy perform. In some embodiments, the brazing material is supplied as a preformed donut shape, similar to braze ring 146 illustrated in FIGS. 5 and 6. In some embodiments, the brazing material to supplied as a wire which may have, for example, a ⅟₃₂″ diameter.

The brazing material may have a high density. In some embodiments, the brazing material has a higher density than needle 136 and horn 144. In these embodiments, horn 144 may be tuned to different resonant frequencies based on the volume of braze material applied. For example, in some embodiments, an ultrasonic debridement system includes a 27 KHz drive signal generator. In this example, the mechanical system may have to resonate between 25 KHz and 29 KHz to function properly. In some cases, if it is determined that stack assembly 138 is resonating at 31 KHz, stack assembly 138 will not function properly. In this example, adding more brazing material can reduce the resonating frequency of stack assembly 138, and therefore enable stack assembly 138 to function properly.

In some embodiments, needle 136 is a fully hardened hypodermic needle which is brazed to horn 144. In some embodiments, needle 136 is connected to horn 144 using a brazing material including silver because silver has a melting point below the annealing point of stainless steal.

In some embodiments, needle 136 is not directly connected to horn 144. For example, needle 136 may be connected to a component which is connected to horn 144. In these embodiments, needle 136 may be described as being operatively connected to horn 144. However, it should be understood that where needle 136 is directly connected to horn 144, needle 136 may be described as being operatively connected to horn 144 also.

In one example embodiment, by brazing needle 136 horn 144, the system described herein may function properly with needle 136 having a length of threes inches and a bore size of 0.035 inches.

Figure 7:
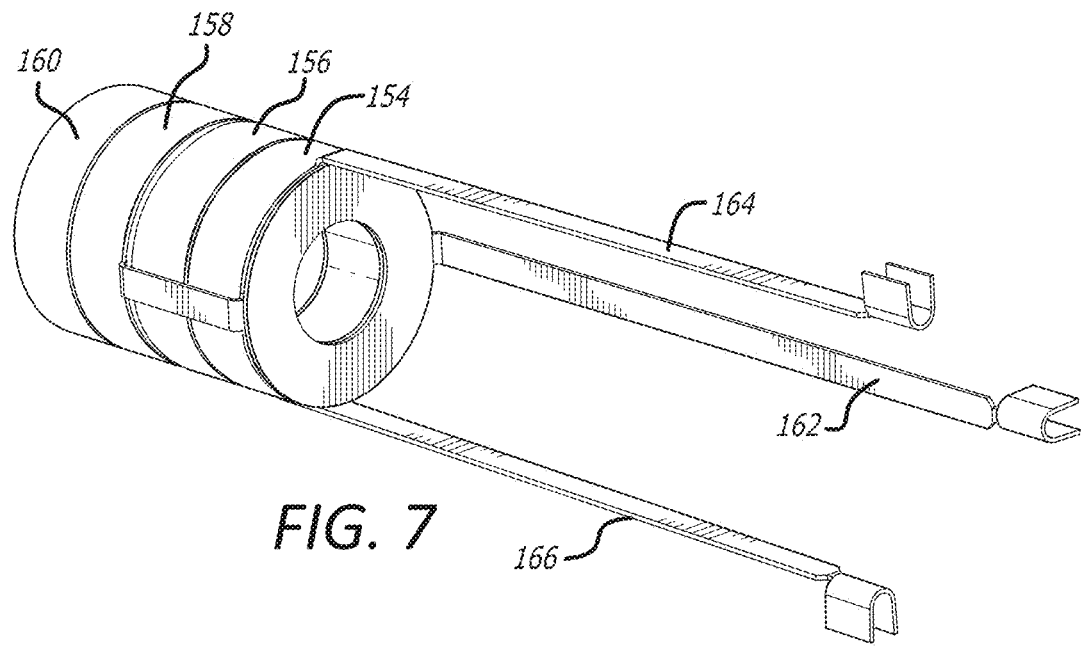
FIG. 7 is a perspective view of an exemplary crystal stack assembly, illustrating the crystal stack assembly having piezoelectric crystals and electrodes.

In some embodiments, crystal stack assembly 142 includes a transducer which is configured to generate ultrasonic energy based on a power signal. For example, as illustrated in FIG. 7, crystal stack assembly 142 includes a transducer which is configured to generate ultrasonic energy based on a power signal which is provided from controller 102. The ultrasonic energy may be applied in a pulsed fashion or continuous fashion.

In some embodiments, the transducer includes piezoelectric crystals. For example, as illustrated in FIG. 7, the transducer includes first piezoelectric crystal 154, second piezoelectric crystal 156, third piezoelectric crystal 158, and fourth piezoelectric crystal 160. In this example, the transducer is operatively connected to first electrode 162, second electrode 164, and third electrode 166.

In some embodiments, the transducer is mounted to mounting member 152 such that ultrasonic energy generated by the transducer is transferred to horn assembly 140. The transducer may be configured to generate longitudinal vibration, transverse vibration, or combinations thereof at desired frequencies. For example, the number and configuration of the piezoelectric crystals may be varied to modify the ultrasonic frequency used for tissue treatment.

As illustrated in FIG. 7, in some embodiments, crystal stack assembly 142 may include four piezoelectric crystals. In some embodiments, crystal stack assembly 142 may include at least two piezoelectric crystals. In some embodiments, as illustrated in FIG. 7, the piezoelectric crystals may be donut-shaped. In some embodiments, as illustrated in FIGS. 2 and 7, the piezoelectric crystals may be configured to receive mounting member and be positioned over mounting member 152.

In some embodiments, the piezoelectric crystals and electrodes are compressed between horn assembly 140 and compressor 168. The piezoelectric crystals may be assembled such that the polarizations are aligned. In some embodiments, portions of the electrodes are sandwiched between the piezoelectric crystals. In some embodiments, the electrodes supply the electric charge to cause these crystals to vibrate.

In some embodiments, as best illustrated in FIG. 7, the ends of electrodes 162, 164 and 166 have a crimping feature which allows for crimping wires to create an electromechanical connection. This type of connection is typically a solder connection. Such a configuration allows for assembly in a dean room without having soldering fumes or acid flux dean up.

In some embodiments, the electrodes include a positive electrode that has a portion that jumps between the positive polarities of the crystals. In some embodiments, the electrodes include negative electrodes that create a safety ground loop circuit. In some embodiments, the negative electrodes are placed between the flat surfaces of the crystals. In these embodiments, the negative electrodes may contact the metal components of the stack to complete the ground circuit.

In some embodiments, compressor 168 is configured to provide compression force for crystal stack assembly 142. Compressor 168 may be torqued to a predetermined value to achieve a specific crystal compression.

Figure 8A:
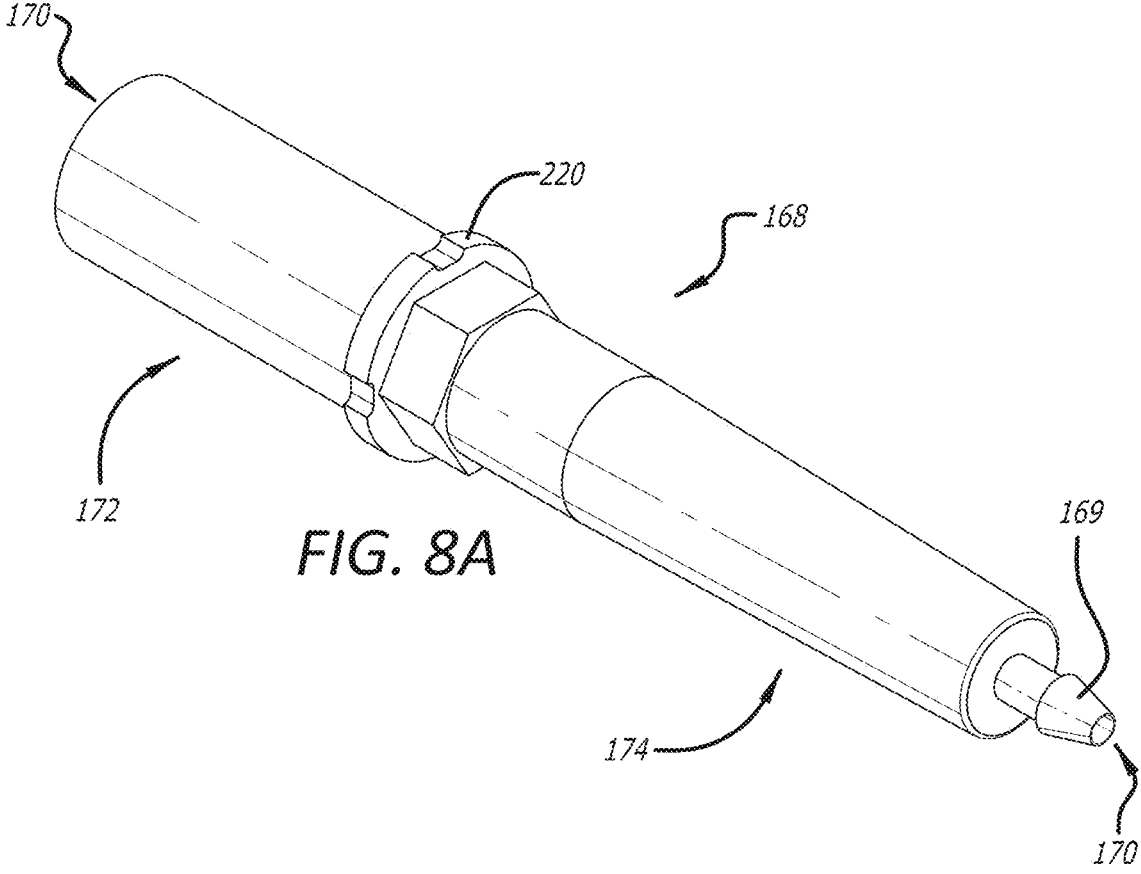
FIG. 8A is perspective view of an exemplary compressor, illustrating the compressor defining a lumen and having a barbed fitting.
Figure 8B:
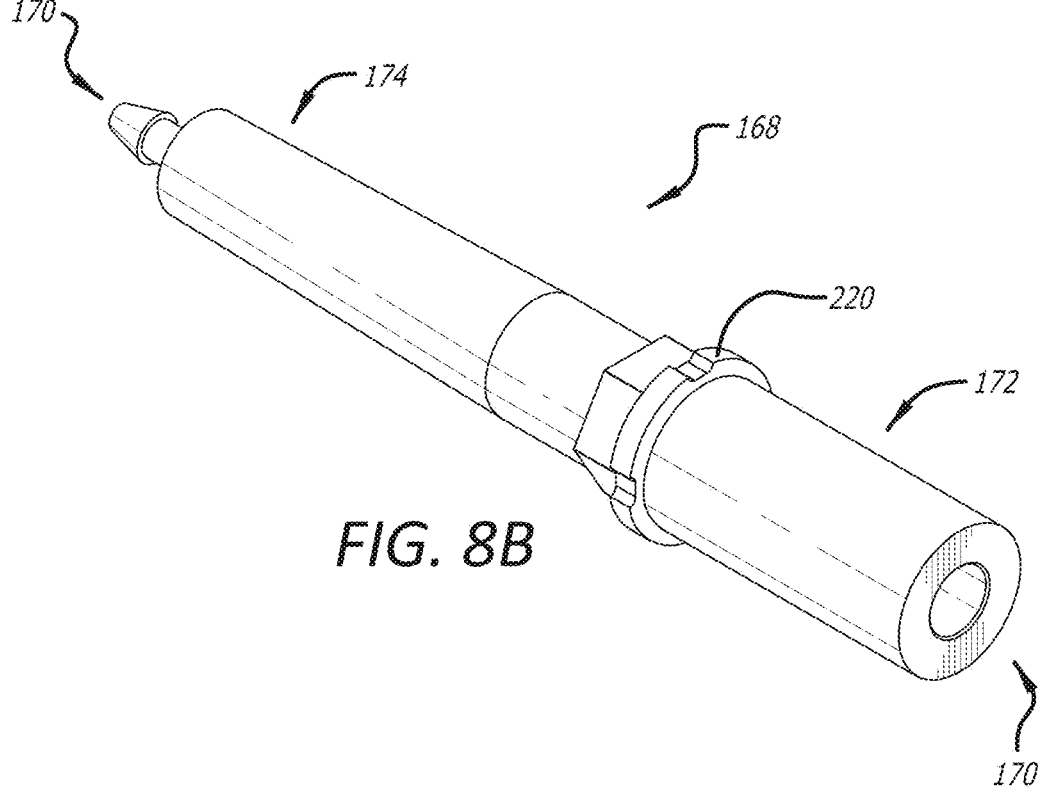
FIG. 8B is another perspective view of the exemplary compressor shown in FIG. 8A.

As illustrated in FIGS. 8 and 9, in some embodiments, compressor 168 may have first end portion 172 and second end portion 174. In some embodiments, compressor 168 defines opening or bore 170 that runs from first end portion 172 to second end portion 174. Opening 170 may be used for directing the aspiration flow to the vacuum line 108.

In some embodiments, compressor 168 may connect to mounting member 152 using any suitable connection method. In some embodiments, first end portion 172 of compressor 168 is connected to mounting member 152 via a threaded connection.

Compressor 168 may include fitting configured to connect to vacuum line 108. For example, as illustrated in FIGS. 8 and 9, compressor 168 includes barb fitting 169 which is configured to connect to vacuum line 108. In this embodiment, barb fitting 169 is integrally formed with compressor 168. In some embodiments, barb fitting is separate from and operably connects to compressor 168. Barb fitting 169 may provide an interference fit with vacuum line 108. Barb fitting 169 may provide for reduced cost of delivery device 102 by eliminating components typically used in the construction of a delivery device. In some embodiments, compressor 168 may be referred to as a compression nut.

In some embodiments, delivery device 102 includes an irrigation conduit that enable delivery device 102 to deliver fluid to a ulcerated wound tissue site, such as beneath an ulcer.

As illustrated in FIG. 9, in some embodiments, the irrigation conduit may be formed by portions of housing 112 and horn assembly 140. More specifically, in some embodiments, the irrigation conduit may formed such that fluid may be passed from the inlet of extension 130, through channel 119 of nose portion 112, and out of sleeve 117 of nose portion 116.

In some embodiments, as best illustrated in FIG. 9, needle 136 and sleeve 117 are secured relative to one another with needle 136 disposed in the inner lumen of sleeve 117. Needle 136 and sleeve 117 define a gap between them to form a portion of the irrigation conduit.

In some embodiments, an outlet from the irrigation conduit may be defined between the terminal end of sleeve 117 and needle 136. Thus, fluid passing into the irrigation conduit in a distal direction passes from the irrigation conduit with fluid generally encircling, or circumscribing the insertion portion of needle 136 and being directed toward the exposed portion of needle 136.

In some embodiments, delivery device 102 includes a vacuum conduit which enables delivery device 102 to remove detritus from the ulcerated wound tissue site.

Referring to FIG. 9, the vacuum conduit may be formed by the lumen portions of: (a) horn assembly 140; (b) mounting member 152; and (c) compressor 168. As illustrated in FIG. 9, the vacuum conduit may be formed by lumens formed in needle 136, horn 144, mounting member 152 and compressor 168.

The vacuum conduit may pass through the transducer as shown in FIG. 9.

In some embodiments, as illustrated in FIG. 9, delivery device 102 includes gasket or O-ring 216. In these embodiments, gasket 216 is configured to fit into groove portion 148 of horn 144. Such a configuration creates a seal between housing 112 and horn 144 such that fluid within the inner compartment formed by nose portion 116 is prevented from entering within body portion 118 and fluid may be delivered through the irrigation conduit.

The length of horn assembly 140—which may include needle 136, horn 144, and grooved portion 148 of horn 144—may be any suitable length. In some embodiments, the length of horn assembly 140 is between about 1.5 inches and about 3.0 inches, between about 1.9 inches and about 2.6 inches, between about 2.1 inches and about 2.5 inches. In some embodiments, the length of horn assembly 140 is between about 2.2 inches and about 2.35 inches, or it is about 2.294 inches.

As illustrated in FIG. 9, delivery device 102 may include gasket 216 disposed between body portion 118 and nose portion 116. In some embodiments, during assembly of delivery device 112, body portion 118 may slide over stack assembly 138 up to and engage gasket 216.

In some embodiments, as illustrated in FIG. 9, delivery device 102 may include gasket or O-ring 218 for creating a seal between mounting member 152 and compressor 168 which may prevent thread lock fluid from running into any piezoelectric crystals. In these embodiments, mounting member 152 may include groove portion 153 as best illustrated in FIG. 6. In this example, gasket 216 is configured to fit into groove portion 153.

In some embodiments, as illustrated in FIG. 9, delivery device 102 may include electrode isolator 220 configure to provide a barrier between compressor 168 and housing 112 and isolate certain electrodes (e.g., a positive electrode) from compressor 168.

Electrode isolator 220 may be configured to isolate compressor 168 from housing 112 during vibration to minimize the effect of the vibration on housing 112 by maintaining electrical and mechanical separation. Electrode isolator 220 may be formed from rubber. Electrode isolator 220 may be configured to be placed in groove 171 of compressor 168.

In some embodiments, tape made with Kapton® polyimide film may be used to electrically isolate the positive electrodes from the ground electrodes and other ground components.

In some embodiments, at each threaded junction, a thread locker is applied to prevent the threads from loosening and to prevent fluid ingress.

In some embodiments, delivery device 102 is a free floating resonator. That is, in this example, delivery device 102 is not fixed such as being fixed to the housing at the tail end. Such a configuration allows for a cost effective manufacture of the delivery device, because, for example, the housing may be formed of a molded plastic material.

In some embodiments, the seal components and vibration isolators are formed of a dampening or insulating material, such as a relatively soft polymeric material, for reducing or inhibiting proximal transmission of ultrasonic energy or other undesirable ultrasonic energy transmission. For example, seal 216 and electrode isolator 220 may be formed of silicone, although a variety of materials are contemplated.

Generally, various components of delivery device 102 contemplated for tissue contact are formed of biocompatible and/or other suitable materials depending upon implementation.

As illustrated in FIG. 1, delivery device 102 may be ergonomically designed, adapted to be hand held (e.g., as a stylet) or otherwise adapted to be manually operated using a single hand. In some embodiments, delivery device 102 may be adapted to be manipulated automatically or semi-automatically (e.g., as part of a robotic system).

In some embodiments, delivery device 102 is pre-tuned to a selected ultrasonic energy frequency or frequency range. For example, an ultrasonic energy frequency range from about 25 kHz to about 29 kHz effectively debrides pathologic tissue located subcutaneously at or around ulcerated wound tissue while reducing the likelihood of trauma to healthy soft tissue.

In operation, the tip portions of needle 136 and sleeve 117 may be percutaneously inserted without having to form an incision in the skin. That is, needle 136 and sleeve 117 may help facilitate atraumatic skin and soft tissue penetration without a need for a separate incision under ultrasonic imaging.

Some methods of delivering ultrasonic energy to target a tissue site include connecting delivery device 102 to a vacuum source, an irrigation source, and a power source of a controller (directly or via a command module). Ultrasonic energy is generated by sending a power signal from the command module to the transducer. The ultrasonic energy is transmitted from the transducer to horn assembly 140 such that the exposed portion of needle 136 delivers ultrasonic energy at a frequency that is pre-selected to debride subcutaneous diseased tissue located at or around an ulcerated wound upon percutaneous insertion of needle 136 and sleeve 117 to target tissue site 300.

In some embodiments, a target tissue comprises pathologic tissue, which may be identified using high frequency ultrasonic imaging. In some embodiments, a user is able to identify a target tissue site entirely at the time of a procedure without cutting the skin of the patient.

As previously described, in some embodiments delivery device 102 is pre-tuned to deliver ultrasonic energy at a frequency that reduces the likelihood of trauma to healthy soft tissue while promoting debridement of the pathologic tissue. The percutaneous, minimally invasive nature of such a procedure facilitates access and treatment of such body tissue as part of a procedure under local anesthesia.

Figure 10A:
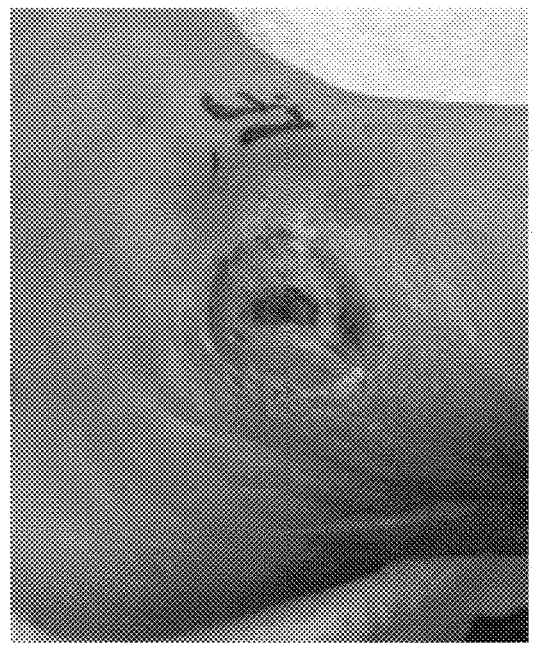
FIGS. 10A-10D comprise intraoperative photos illustrating a technique of percutaneous ultrasonic debridement via adjacent percutaneous portals according to the present disclosure.
Figure 10B:
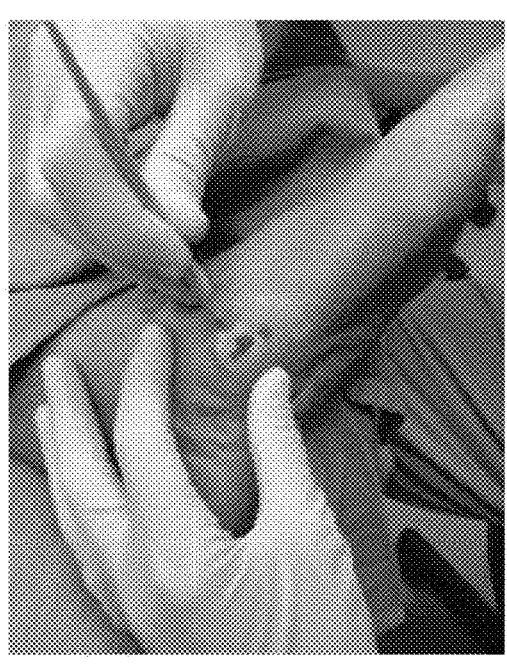
Figure 10C:
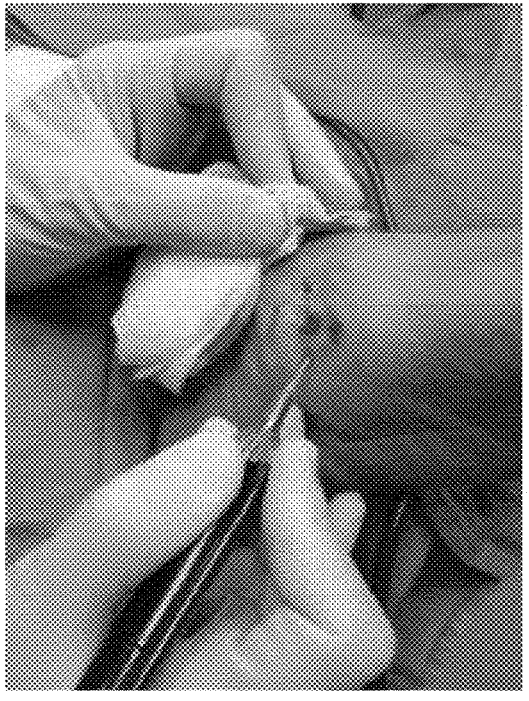
Figure 10D:
Figure 11A:
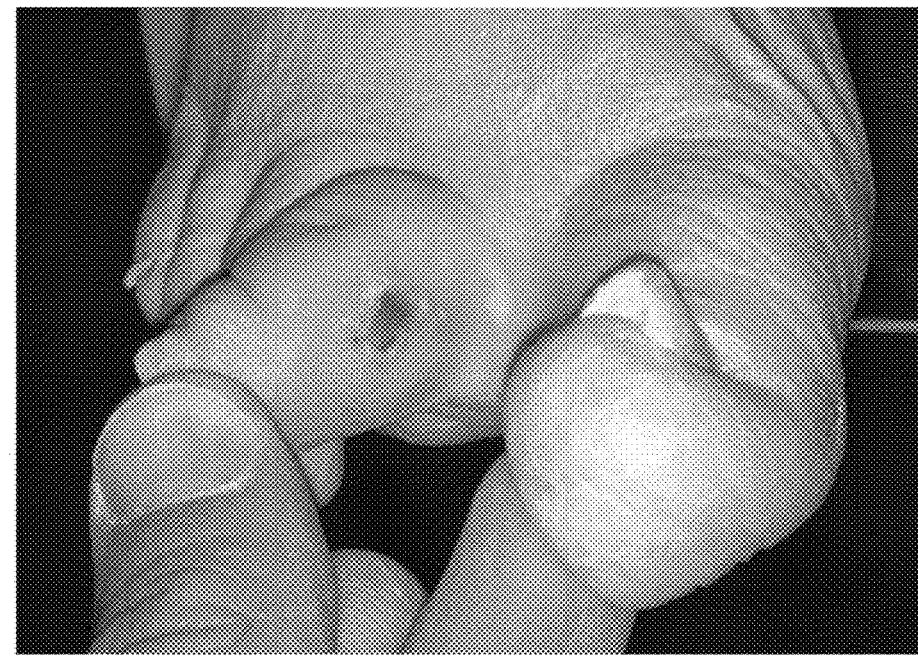
FIGS. 11A-11B illustrate an interdigital ulcer on the right 2.sup.nd digit before and after an ultrasonic debridement treatment performed according to the present disclosure.
Figure 11B:
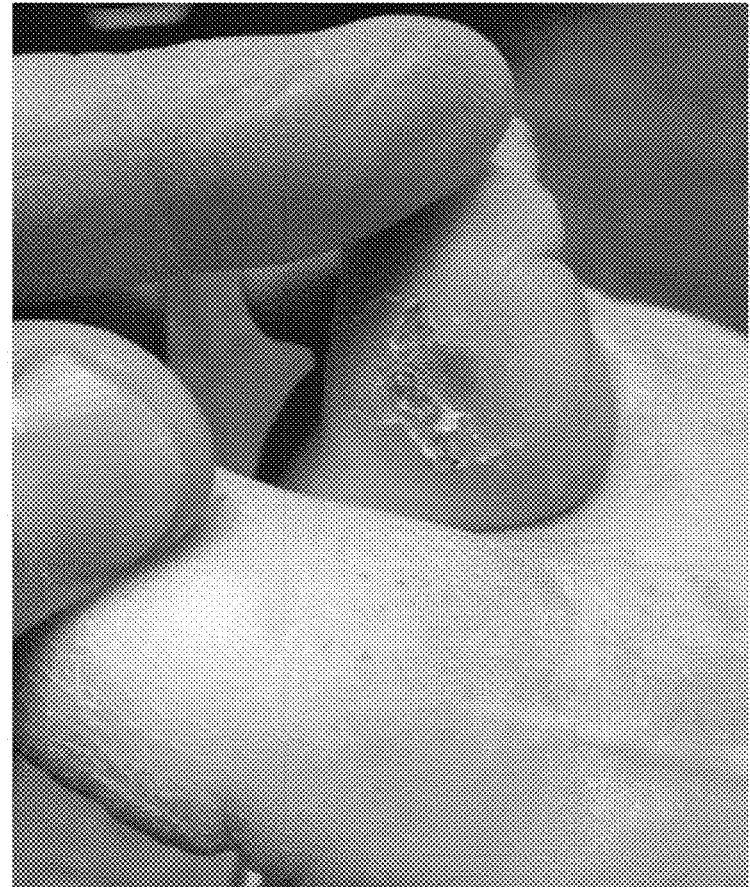
Figure 12A:
FIGS. 12A-12B illustrate a left plantar 1.sup.st metatarsal ulcer before and after an ultrasonic debridement treatment performed according to the present disclosure.
Figure 12B:
Figure 14A:
FIGS. 14A-14B illustrate a left central forefoot ulcer with significant problematic bursa before and after an ultrasonic debridement treatment performed according to the present disclosure.
Figure 14B:
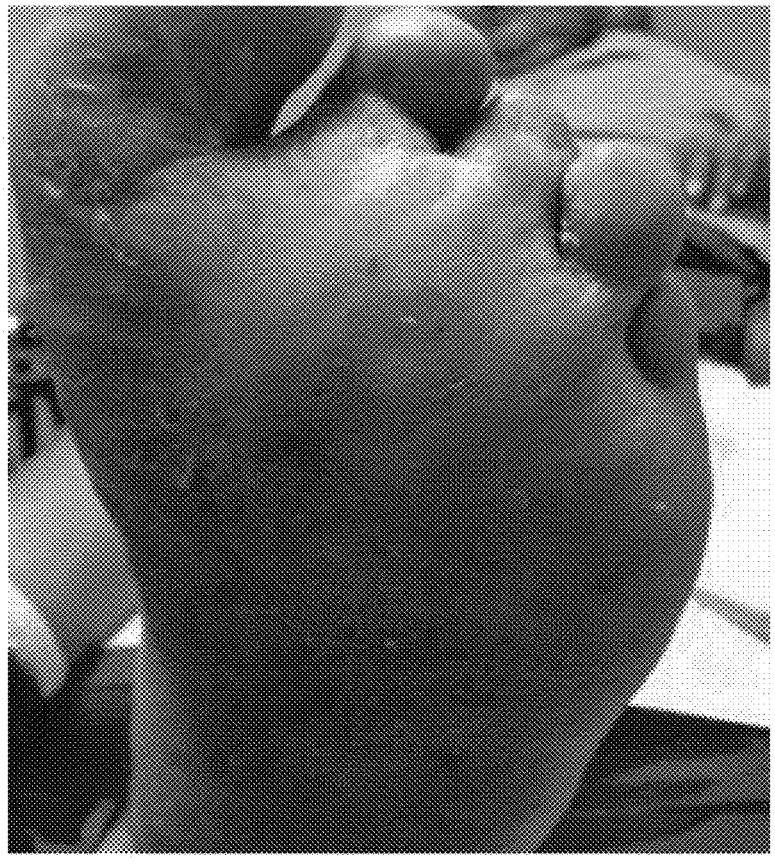
Figure 15A:
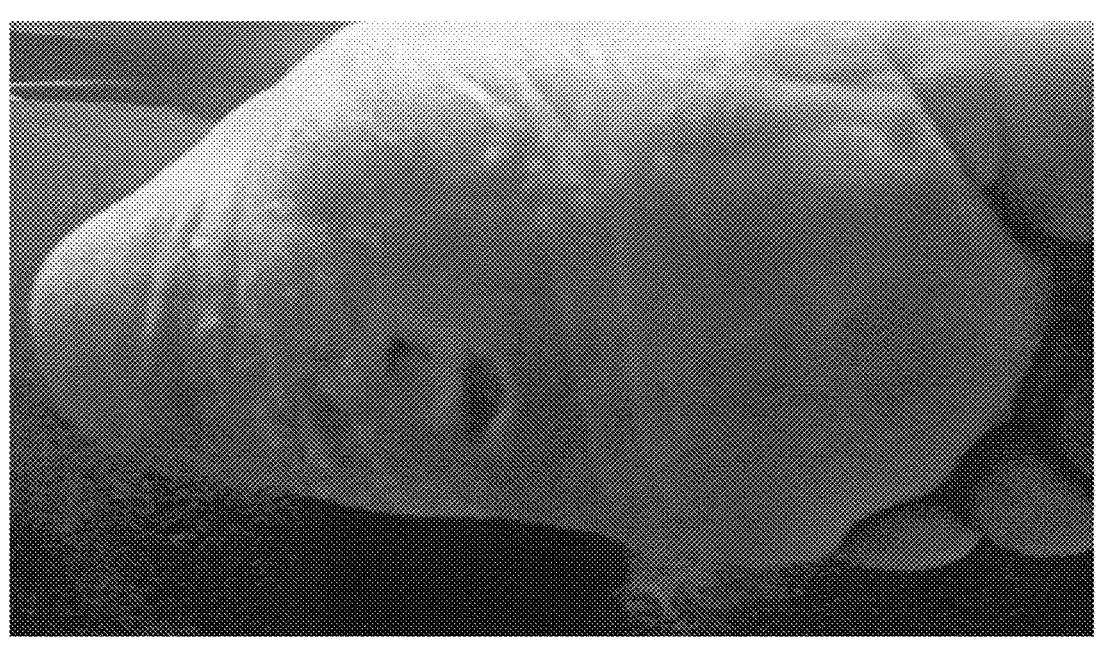
FIGS. 15A-15B illustrate a left Charcot midfoot ulcer before and after an ultrasonic debridement treatment performed according to the present disclosure.
Figure 15B:
Figure 17A:
FIGS. 17A-17D illustrate the left foot of patient with midfoot Charcot deformity with severe C-shaped foot and two ulcerations before and after an ultrasonic debridement treatment performed according to the present disclosure.
Figure 17B:
Figure 17C:
Figure 17D:
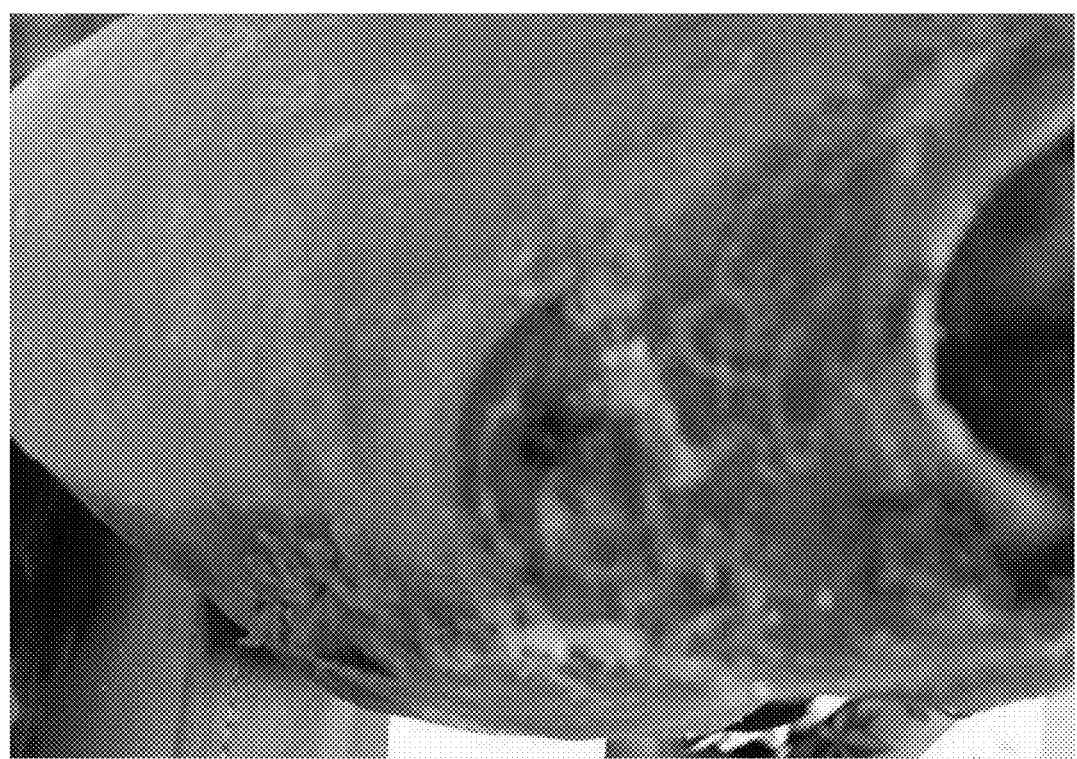

FIGS. 10A-D comprise intraoperative photos illustrating a technique of percutaneous ultrasonic debridement via adjacent percutaneous portals according to the present disclosure. FIG. 10A illustrates a wound prior to performing a procedure outlined in the present description. In some embodiments, external hyperkeratosis is debrided prior to performing an ultrasonic debridement procedure. Following administration of local anesthesia, the wound is prepped and draped in typical fashion using sterile technique. FIGS. 10B-D illustrate a processes of using a 15 blade to create access portals via small stab incisions in a cardinal orientation. Larger wound sizes may necessitate additional portals at intercardinal points as well. FIG. 10C also illustrates the hand piece being used to debride targeted abnormal tissue below the external tissue of a foot ulcer. FIG. 10D illustrates the wound shown in FIGS. 10A-10C immediately following the debridement procedure. In this image, four cardinal access portals can be seen around the ulcer. According to some embodiments, a sterile dressing is applied immediately after or shortly after the debridement procedure is completed.

After performing a percutaneous debridement procedure according to the present disclosure, the wound will require time to heal. The amount of time may depend on the severity and/or size of the wound prior to treatment. In some cases, the healing time will be between about 0 and about 10 weeks, between about 0.5 and about 5 weeks, or between about 1 and about 3 weeks. In some cases, the healing time will be between about 1 and 2 weeks.

Exemplary Use of Subcutaneous Debridement in Foot Ulcers

A pilot assessment of percutaneous ultrasonic debridement of subcutaneous diseased tissue on chronic refractory neuropathic pedal ulcerations was conducted utilizing the equipment and techniques disclosed herein. Twelve patients were treated with percutaneous ultrasonic debridement using a device according to the present disclosure. The average time of wound prior to treatment was 109.2 weeks. Of the twelve patients, ten (or about 83%) healed in under two weeks (average time to healing 1.44 weeks) and without recurrence (average follow up time 24.75 weeks). Average cost estimation of prior treatments was $33,306.50 per patient compared to one in-office percutaneous procedure at a cost of about $1,200 or in an ambulatory surgery center at a cost of about $2,500. This study exhibited the favorable healing time, significant lack of recurrence in ulcerations, and cost savings achievable with the devices and methods of the present disclosure.

Patients and Methods

The records of twelve consecutive patients were reviewed. Each patient had neuropathic ulcerations treated with percutaneous ultrasonic treatment. These recalcitrant wounds were noted to have failed conservative therapy for a minimum of five months. The percutaneous intervention was discussed on multiple previous office visits and performed either in an ambulatory surgical center treatment room or in the office of the senior author (LHF).

The Device

The instrument—a device according to the present disclosure—delivers ultrasonic energy and simultaneously fragments and aspirates the treated subcutaneous tissue. Constant irrigation provides a safety measure to avoid thermal injury to normal tissue.

Technique

Local anesthetic was administered to anesthetize the area of concern. The foot was prepped and draped. The visual ultrasound probe was prepped if performing under visual guidance. If so, vital structures were identified. The percutaneous ultrasonic needle (16 gauge) was advanced into the pathologic region via multiple access points. One technique is to position access portals in the intact skin adjacent to the wounds at cardinal points, adding intercardinal points for larger wounds. See FIGS. 10A-10D Using the needle tip, ultrasonic energy is imparted at a specific frequency (between about 25 kHz and 29 kHz) designed to debride and aspirate the targeted abnormal tissue, both soft and hard tissue (i.e., bone) at the same time. The tool and needle also provide irrigation and aspiration to effectively remove diseased and infected tissue. The single use needle and instrument was maneuvered along the region of the ulcerated wound with or without a boney prominence until resolved. If ultrasonic imaging is indicated, it was used concomitantly in the non-dominant hand to visualize positioning of the instrument.

Following the procedure, a sterile dressing was applied to the wound and portal sites. Daily dressings and non-weight-bearing status were then initiated.

Of the twelve patients treated with percutaneous ultrasonic debridement during the study period, none were excluded. The twelve patients provided thirteen ulcers on twelve affected feet, with one patient having two ulcerations in close proximity (lateral midfoot) that were both treated. The average time of wound prior to treatment was 109.2 weeks. Of the twelve patients, ten (83%) healed in under two weeks (average time to healing 1.44 weeks) and without recurrence (average follow up time 24.75 weeks). FIGS. 12-17 illustrate the before and after images of the various ulcerated wounds.

With percutaneous ultrasonic treatment of the subcutaneous tissue at or around the ulcerated wound, functional ambulation without recurrence is a realistic goal. This technique has proven effective across a wide range of anatomic locations in the foot: the heel, the Charcot midfoot, the plantar 1st metatarsalphalangeal joint, the planter central metatarsalphalangeal joint, the hallux, and the interdigital pedal location. Ten of the twelve (83%) consecutive cases healed without recurrence.

In wounds that occur more proximally or in areas near vital neurovascular structures, use of visual ultrasound guidance may help avoid those structures and potential adverse sequelae.

Although the present disclosure has been described with reference to various examples, persons skilled in the art will recognize that changes may be made in form and detail without departing from the spirit and scope of the present disclosure. For example, various modifications and additions can be made to the exemplary embodiments discussed without departing from the scope of present disclosure. While the embodiments described above refer to particular features, the scope of the present disclosure also includes embodiments having different combinations of features and embodiments that do not include all of the above described features.

What is claimed is:

1. A system configured for percutaneously treating a target wound tissue, the system comprising:
   a transducer;
   a horn; and
   a fully hardened needle fixed to the horn, the needle comprising an exposed portion having a length of about 0.75 inches to about 3.0 inches,
      wherein a distal portion of the needle is configured to be inserted into a first position subcutaneous to the target wound tissue using a first access portal and then inserted into a second position subcutaneous to the target wound tissue using a second access portal, and
      wherein the horn and transducer are configured to generate ultrasonic energy at the first subcutaneous position and
      at the second subcutaneous position.

2. The system of claim 1, wherein the system is further configured to debride the target wound tissue with the ultrasonic energy.

3. The system of claim 2, further comprising an aspiration conduit configured to remove from at least one of the first subcutaneous position or the second subcutaneous position at least some detritus that may have been produced by the debriding.

4. The system of claim 1, further comprising an irrigation conduit configured to deliver fluid to at least one of the first subcutaneous position or the second subcutaneous position.

5. The system of claim 1, wherein the ultrasonic energy is delivered through the needle.

6. The system of claim 1, further comprising a rigid sheath around at least a section of the needle.

7. The system of claim 6, wherein the sheath includes an inner lumen forming a part of an irrigation conduit.

8. The system of claim 6, wherein the sheath includes an insertion portion configured to be inserted into the target wound tissue.

9. The system of claim 1, further comprising a cap configured to removably cover the needle.

10. The system of claim 9, further comprising a housing, wherein the cap is removably connectable to the housing.

11. The system of claim 1, wherein the needle comprises a stainless steel material, and wherein the needle is brazed to the horn.

12. The system of claim 1, wherein the needle is a hypodermic needle.

13. The system of claim 1, wherein the needle has a gauge of about 12 to about 25.

14. A system configured for percutaneously treating a target wound tissue, the system comprising:
   a transducer;
   a horn; and
   a fully hardened needle having a bevel at a distal tip, the needle comprising an exposed portion having a length of about 0.75 inches to about 3.0 inches,
      wherein a distal portion of the needle is configured to be inserted into a first position subcutaneous to the target wound tissue and then inserted into a second position subcutaneous to the target wound tissue, and
      wherein the horn and the transducer are configured to generate ultrasonic energy at the first subcutaneous position and
      at the second subcutaneous position.

15. The system of claim 14, wherein the needle bevel is about 45 degrees.

16. The system of claim 14, further comprising a rigid sheath around at least a section of the needle.

17. The system of claim 16, wherein the sheath includes an inner lumen forming a part of a fluid conduit.

18. The system of claim 14, further comprising a cap configured to removably cover the needle.

19. The system of claim 18, further comprising a housing, wherein the cap is removably connectable to the housing.

* * * * *